(12) United States Patent
Yagi et al.

(10) Patent No.: US 7,922,652 B2
(45) Date of Patent: Apr. 12, 2011

(54) ENDOSCOPE SYSTEM

(75) Inventors: Yasushi Yagi, Hyogo (JP); Tomio Echigo, Osaka (JP); Ryusuke Sagawa, Osaka (JP)

(73) Assignee: Osaka University, Osaka (JP)

( * ) Notice: Subject to any disclaimer, the term of this patent is extended or adjusted under 35 U.S.C. 154(b) by 1289 days.

(21) Appl. No.: 10/587,881

(22) PCT Filed: Feb. 17, 2005

(86) PCT No.: PCT/JP2005/002416
§ 371 (c)(1),
(2), (4) Date: Aug. 1, 2006

(87) PCT Pub. No.: WO2005/077253
PCT Pub. Date: Aug. 25, 2005

(65) Prior Publication Data
US 2007/0161853 A1    Jul. 12, 2007

(30) Foreign Application Priority Data
Feb. 18, 2004    (JP) ................................. 2004-041209

(51) Int. Cl.
*A61B 1/04* (2006.01)
(52) U.S. Cl. ...................................................... 600/109
(58) Field of Classification Search .................. 600/103, 600/109, 117, 170; 382/294–296
See application file for complete search history.

(56) References Cited

U.S. PATENT DOCUMENTS

| 6,081,740 | A * | 6/2000 | Gombrich et al. | ............ 600/424 |
| 2002/0103420 | A1 * | 8/2002 | Coleman et al. | ............ 600/173 |
| 2003/0045790 | A1 | 3/2003 | Lewkowicz et al. | |
| 2003/0191369 | A1 * | 10/2003 | Arai et al. | ............ 600/173 |
| 2004/0210105 | A1 * | 10/2004 | Hale et al. | ............ 600/101 |

(Continued)

FOREIGN PATENT DOCUMENTS

DE    103 18 205    11/2004

(Continued)

OTHER PUBLICATIONS

Heung-Yeung Shum and R. Szeliski, "Construction and Refinement of Panoramic Mosaics with Global and Local Alignment," Proc. Int'l Conf. Computer Vision, pp. 953-958, 1998.*

(Continued)

*Primary Examiner* — Philip R Smith
(74) *Attorney, Agent, or Firm* — Wenderoth, Lind & Ponack, L.L.P.

(57) ABSTRACT

An endoscope that is free from a dead area and capable of preventing the physician from overlooking any nidus is an endoscope for taking the inside of digestive organs, and the endoscope is provided with an omnidirectional camera (32), a light (34), a forceps (36) and a rinse water injection port (38) at the tip (24). The omnidirectional camera (32) is a device for taking the inside of digestive organs, and is able to take 360-degree images of its surroundings. A probe-type endoscope (20) is provided with a receiver (26) composed of orthogonal coils, and the receiver (26) is used for estimating the position and attitude of the probe-type endoscope (20). An image taken by the omnidirectional camera (32) is presented on a display unit (28) of an image processing device (22) connected to the probe-type endoscope (20). In the image processing device, a video mosaicking process is performed on a plurality of images obtained by the omnidirectional camera (32) to generate a panoramic image of the inside of a digestive organ.

9 Claims, 14 Drawing Sheets

U.S. PATENT DOCUMENTS

| | | | | |
|---|---|---|---|---|
| 2004/0249247 | A1* | 12/2004 | Iddan | 600/170 |
| 2004/0264754 | A1 | 12/2004 | Kleen et al. | |
| 2005/0165276 | A1* | 7/2005 | Belson et al. | 600/146 |
| 2006/0106283 | A1* | 5/2006 | Wallace et al. | 600/109 |
| 2006/0217593 | A1* | 9/2006 | Gilad et al. | 600/160 |
| 2007/0073103 | A1* | 3/2007 | Akizuki | 600/109 |

FOREIGN PATENT DOCUMENTS

| | | |
|---|---|---|
| JP | 2004-321796 | 11/2004 |
| JP | 2005-501630 | 1/2005 |
| WO | 03/021529 | 3/2003 |

OTHER PUBLICATIONS

Pless, R., T. Brodsky, and Y. Aloimonos, "Detecting Independent Motion: The Statistics of Temporal Continuity," IEEE Transactions on Pattern Analysis and Machine Intelligence, vol. 22, No. 8, Aug. 2000.*

Steedly, D., C. Pal, and R Szeliski, "Efficiently Registering Video into Panoramic Mosaics," Proc. Int'l Conf. Computer Vision, pp. 1300-1307, vol. 2, Dec. 2005.*

"M2A® Capsule Endoscopy Given® Diagnostic System", [online], Given Imaging Ltd., [searched on Feb. 4, 2004], Internet <URL: http://www.givenimaging.com/NR/rdonlyres/76C20644-4B5B-4964-811A-071E8133F83A/0/GI_Marketing_Brochure_2003.pdf>.

H. Sawhney et al., "Compact Representations of Videos Through Dominant and Multiple Motion Estimation," IEEE Transactions on Pattern Analysis and Machine Intelligence 18(8), pp. 814-830, 1996.

A. Bartoli et al., "Motion Panoramas," INRIA Research Report RR-4771, Mar. 2003.

C. Tomasi et al., "Shape and Motion from Image Streams under Orthography: A Factorization Method," IJCV, 1992, vol. 9, No. 2, pp. 137-154.

L. Torresani et al., "Tracking and Modeling Non-Rigid Objects with Rank Constraints," In Proc. CVPR, 2001, vol. I, pp. 493-500.

O. Faugeras et al., "Camera self-calibration: theory and experiments," in G. Sandini (ed.), Proc $2^{nd}$ ECCV, 1992, vol. 588 of Lecture Notes in Computer Science, Springer-Verlag, Santa Margherita Ligure, Italy, pp. 321-334.

Marc Pollefeys, University of North Carolina-Chapel Hill, U.S.A., "Visual 3d Modeling from Images", http://www.cs.unc.edu/~marc/tutorial/, Nov. 2002.

Marc Pollefeys et al., *Visual Modeling with a Hand-Held Camera,* http://portal.acm.org/portal.cfm,2004.

Kazumasa Yamazawa et al., "Omnidirectional Visual Sensors for Navigation of Mobile Robots", Journal of the Institute of Electronics, Information and Communication Engineers, D-II, vol. J79-D-II, No. 5, pp. 698-707 (May 1996).

* cited by examiner

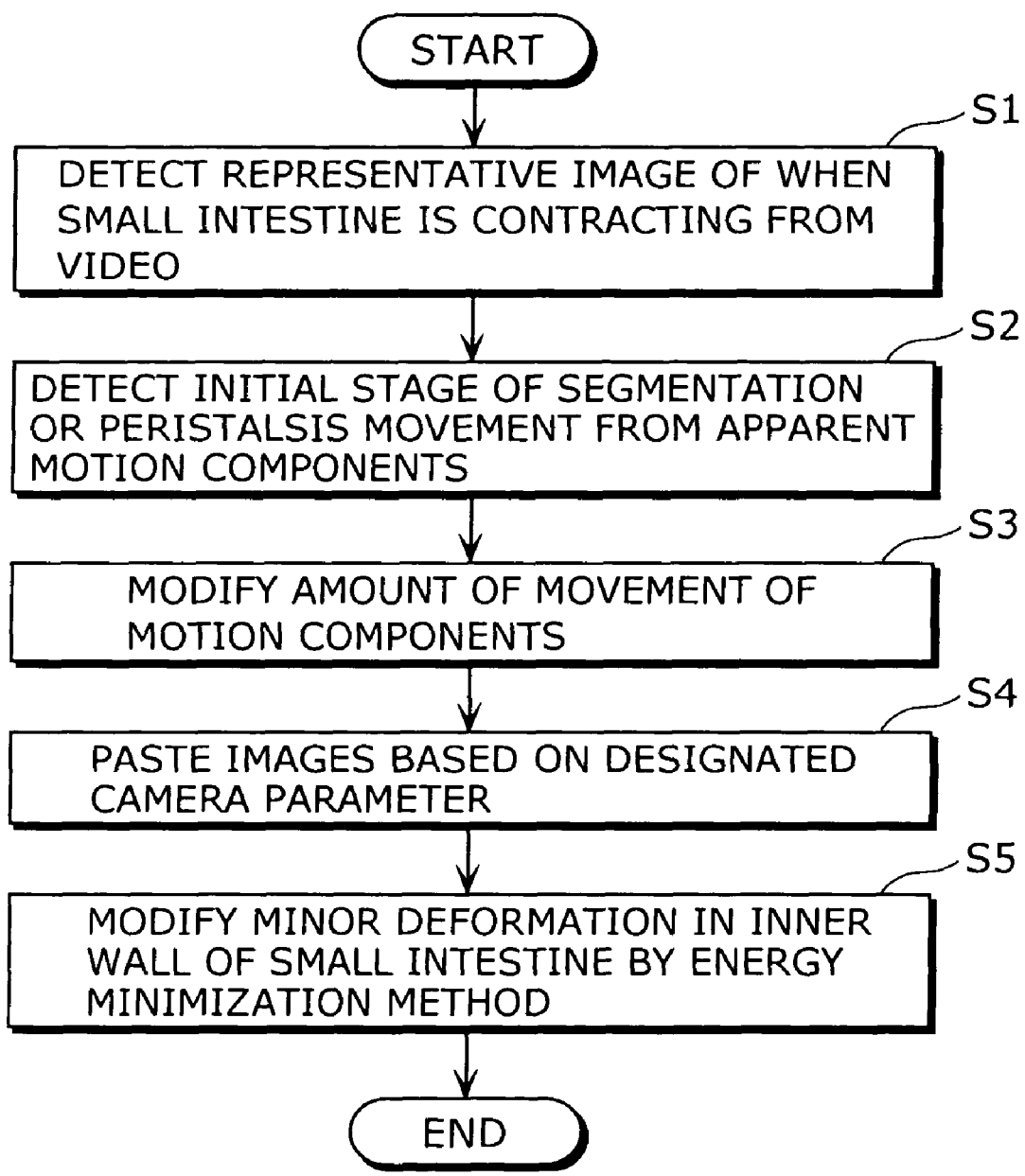

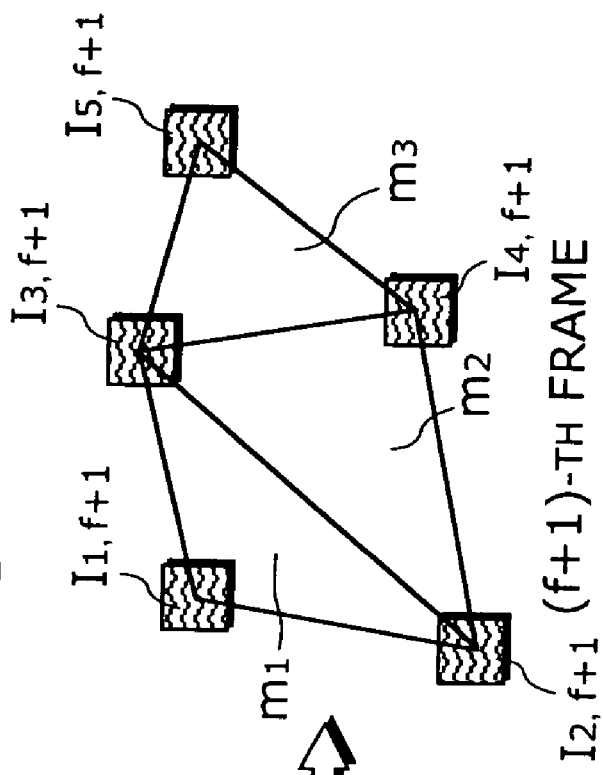
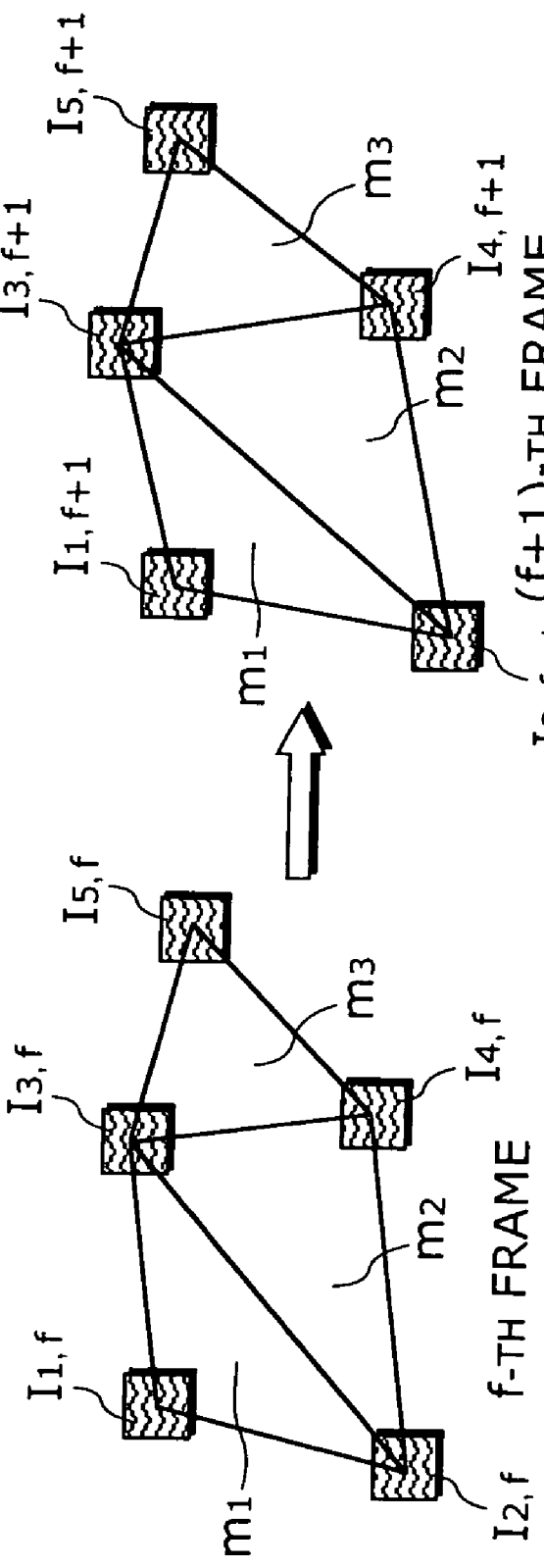
FIG. 17A
FIG. 17B

FIRST FRAME

SECOND FRAME

ENDOSCOPE SYSTEM

TECHNICAL FIELD

The present invention relates to endoscopes and endoscope systems and, in particular, to an endoscope and an endoscope system for observing the inside of the digestive organs.

BACKGROUND ART

Conventionally, in the field of medical practice, probe-type endoscopes are used for examining the digestive organs. The endoscopic probe has a camera, a light, a forceps and a rinse water injection port mounted to its tip. The physician inserts the probe through the oral cavity or the anus into a digestive organ, and carries out diagnosis, collection of a lesion and treatment, while monitoring video obtained by the camera at the tip.

With an endoscope inserted from the oral cavity, examination and treatment of the esophagus, stomach and duodenum are carried out, whereas with an endoscope inserted from the anus, examination and treatment of the rectum and large intestine are carried out. However, the small intestine of an adult male is as long as about 3 m, and therefore it is difficult to insert the probe into the small intestine. For this reason, existing endoscopes are not used for examining the small intestine.

Therefore, it is expected that a new examination approach for the small intestine will be proposed. As a promising method therefor, a capsule endoscope is expected (for example, see Non-patent Reference 1). As for the capsule endoscope, in the west, 40,000 clinical experiments have been conducted so that attention is paid thereto, whereas in Japan, it is still at the stage of awaiting approval as a medical instrument.

The capsule endoscope is intended to keep taking video of the digestive organs over several hours with an encapsulated camera since the camera is swallowed by a subject until it passes from the stomach through the small intestine to the large intestine for ejection. The capsule endoscope is expected to be considerably effective in observing the small intestine, although treatment therewith is difficult. In addition, after swallowing the capsule, it is possible to lead normal life, therefore the burden of examination imposed on the subject is less compared to conventional endoscopes, and further diffusion of the endoscopic examination is anticipated.

Described below is the general background art of image processing relevant to the present invention.

[Video Mosaicking]

Video mosaicking is known as a technique for, in the video taking with a camera that involves motion, detecting motion components of the camera based on features of adjacent images and pasting the images to generate a still image. Video mosaicking is standardized as a sprite compression method in MPEG (Moving Picture Experts Group)-4, which is an international standard for video coding. In this approach, motion parameters of a camera are detected by detecting how a feature point in an image has moved between adjacent frames. As this approach, there are an approach that assumes camera motion as dominant motion in order to distinguish between a moving feature point and an apparent movement of the feature point due to the camera motion (for example, see Non-patent Reference 2), an approach that separates an image into two types of regions making up the foreground and background and detects motion parameters of a camera from the background (for example, see Non-patent Reference 3), and so on.

[Simultaneous Estimation of Camera Motion and Three-Dimension Information]

In addition, a method for, in the video taking that involves camera motion, simultaneously detecting camera motion parameters and three-dimension information of a scene from an image sequence therefor is known as Structure From Motion (SFM). One approach of the SFM takes, as an observation matrix, a series of a plurality of feature points generated by camera motion, and utilizes the nature that a target still scene is rank-3 constrained in the result obtained by a factorization method. Based on this, there has been proposed an approach that detects camera motion and three-dimension information (for example, see Non-patent Reference 4). In addition, there has been proposed an approach that extends such approach to linearly combine a plurality of three-dimensional structures and thereby to acquire three-dimension information for a scene that is to be deformed (for example, see Non-patent Reference 5).

In addition, regarding the problem of estimating the motion of a moving camera from an obtained image sequence, it is indicated that corresponding feature points in two images obtained from different viewpoints can be expressed in a fundamental matrix under the epipolar constraint, and motion parameters can be estimated based on seven or more pairs of feature points (for example, see Non-patent Reference 6). Further, a method called bundle adjustment, which uses a number of images to adjust previously obtained positions of a camera and feature points to accurate values, is used in the field of photogrammetry (for example, see Non-patent Reference 7).

[Acquisition of Camera Position Information]

In addition, there are endoscopes having a sensor mounted thereto in order to sense the position of a camera. As for the capsule endoscope, there is a technique developed for receiving video sent from the capsule endoscope at a plurality of antennae to acquire position information of the capsule within the body.

Non-patent Reference 1: "M2A (R) Capsule Endoscopy Given (R) Diagnostic System", [online], Given Imaging Ltd., [searched on Feb. 4, 2004], Internet <URL: http://www.givenimaging.com/NR/rdonlyres/76C20644-4B5B-4964-811A-071 E8133F83A/0/GI_Marketing_Brochure_2003.pdf>

Non-patent Reference 2: H. Sawhney, S. Ayer, "Compact Representations of Videos Through Dominant and Multiple Motion Estimation," IEEE Transactions on Pattern Analysis and Machine Intelligence 18(8), pp. 814-830, 1996.

Non-patent Reference 3: A. Bartoli, N. Dalal, and R. Horaud, "Motion Panoramas," INRIA Research Report RR-4771

Non-patent Reference 4: C. Tomasi and T. Kanade, "Shape and Motion from Image Streams under Orthography: A Factorization Method," IJCV, vol. 9, no. 2, pp. 137-154, 1992.

Non-patent Reference 5: L. Torresani, D. B. Yang, E. J. Alexander, and C. Bregler. "Tracking and Modeling Non-Rigid Objects with Rank Constraints," In Proc. CVPR, vol. I, pp. 493-500, 2001.

Non-patent Reference 6: O. Faugeras, T. Luong, and S. Maybank, "Camera self-calibration: theory and experiments," in G. Sandini (ed.), Proc 2nd ECCV, Vol. 588 of Lecture Notes in Computer Science, Springer-Verlag, Santa Margherita Ligure, Italy, pp. 321-334, 1992.

Non-patent Reference 7: D. Brown. "The bundle adjustment—progress and prospect." In XIII Congress of the ISPRS, Helsinki, 1976.

DISCLOSURE OF INVENTION

Problems that Invention is to Solve

However, although existing endoscopes are suitable for insert operations because the forward field of view of a camera is open for inserting the probe, there is a concern that a lesion might be overlooked because the wall surface of a digestive organ that is to be actually diagnosed lies on the side of the probe and corresponds to a peripheral portion of video taken with a super wide angle lens, making it difficult for the physician to observe it.

In addition, the capsule endoscope has a field of view in front of the capsule as in the conventional probe-type endoscope, and takes video while the capsule is moving through the digestive organs, but the capsule is not provided with the function of controlling its direction, and therefore in some cases, the camera having a forward field of view might not be able to take images of all inner walls of the digestive organs. As a result, there arises a critical problem leading to an overlook in the examination.

In addition, the capsule endoscope carries out an examination while reproducing temporarily recorded video because the capsule spends about eight hours to pass through the digestive organs. Accordingly, the method for diagnosing the digestive organs by the capsule endoscope employs a process that observes images one by one. Thus, the time required for the physician to carry out medical practice becomes a considerable burden.

On the other hand, generation of three-dimensional images of the intestines by using CT (computerized tomography) was discussed as an approach for modeling the entirety of the intestinal tracts, but it is inferior in performance compared to the endoscopes because a small lesion and a flat lesion cannot be detected.

The present invention has been made to solve the above-described problems, and a first object thereof is to provide an endoscope system capable of preventing the physician from overlooking any nidus.

In addition, a second object is to provide an endoscope system for improving the physician's diagnostic efficiency.

Means to Solve the Problems

To attain the above objects, an endoscope system according to an aspect of the present invention is an endoscope system for taking images of the inside of an object, including: a camera which takes images of the inside of the object in a living body, which is capable of motion; and an image generation unit which generates a panoramic image of the inside of the object by performing a video mosaicking process, a motion correction process, and an image modification process intended for pasting the images through energy minimization on the plurality of images obtained by the camera, estimating camera motion, correcting previously definable motion in the living body and correcting previously indefinable internal deformation in the living body.

With this structure, it is possible to take images of the inside of a movable object in a living body, and perform a video mosaicking process to generate a panoramic image of the inside of the object. As a result, it is possible to generate a panoramic image of the inside of a movable object in a living body such as the inner wall of a digestive tract. As such, even in the case where a shooting target moves, it is possible to create a panoramic image. Therefore, it is made possible to intensively observe the inner wall of the digestive tract and so on, and prevent the physician from overlooking any nidus. In addition, the physician is not required to spend a long period of time keeping observing images of the inner wall of the digestive tract. Thus, it is possible to improve the physician's diagnosis efficiency.

In addition, the image generation unit may include a motion estimation unit which estimates the motion of the camera based on the images of the inside of the object taken by the camera, and a panoramic image generation unit which generates a panoramic image of the inside of the object from the images taken by the camera based on the estimation result of the motion of the camera.

In addition, the motion estimation unit may include a corresponding point detection unit which expresses an observation point of the camera in a spherical coordinate system and detects corresponding points for the observation point from the plurality of images obtained by the camera, and a motion parameter estimation unit which estimates a motion parameter expressing the motion of the camera based on a plurality of the corresponding points.

In addition, the motion estimation unit may include a camera motion estimation unit which estimates the motion of the camera from two temporally different images obtained by the camera by using an epipolar constraint condition, and a camera motion correction unit which corrects the motion of the camera estimated by the camera motion estimation unit by performing a bundle adjustment process using the plurality of temporally different images obtained by the camera. Preferably, the camera motion correction unit performs the bundle adjustment process by approximating a change inside the object due to segmentation movement by a sine wave.

As such, by approximating a change of the inner wall of a digestive organ due to the segmentation movement by such sine wave, it is made possible to obtain more accurate camera motion and, moreover, to obtain a more accurate panoramic image, thereby preventing the physician's erroneous diagnosis.

More preferably, the camera motion correction unit performs the bundle adjustment process by approximating a change inside the object due to peristalsis movement by movement of a soliton.

As such, by approximating the change inside the object due to the peristalsis movement by movement of a soliton, it is made possible to obtain more accurate camera motion, and moreover, to obtain a more accurate panoramic image, thereby preventing the physician's erroneous diagnosis.

More preferably, the object is a cylindrical object, and the panoramic image generation unit generates a cylindrical-shaped model of the object and fits the plurality of images obtained by the camera to the cylindrical-shaped model based on a feature point used at the time of estimating the motion.

By generating such cylindrical-shaped model of the digestive organs, it is possible to obtain panoramic images of the digestive organs with a cylindrical shape, such as the small intestine and the large intestine, to generate their spread images. As a result, it is made possible for the physician to carry out diagnosis accurately and efficiently. In particular, as for the capsule endoscope, which spends about eight hours to take images, an enormous amount of image data can be obtained. Therefore, by obtaining movement parameters of the camera from the enormous amount of image data, and pasting the images onto an approximated geometric shape, overlapping and redundant information is deleted so that only effective images are rendered. Thus, more efficient consultation is made possible.

In addition, the above-described endoscope system may further include a position/attitude sensor which measures a self-position or attitude, and the motion estimation unit may estimate the motion of the camera in consideration of the measurement result by the position/attitude sensor.

While the estimation of camera motion from images normally attains accuracy suitable for panorama generation, there is often a risk of making a critical error. Accordingly, by additionally using the position/attitude sensor to prevent a critical error with the sensor, and relying on image processing for detail work, it is made possible to generate panoramic images with high accuracy and at high speed.

More preferably, the image generation unit includes a feature region cutout unit which cuts out a plurality of feature regions having a predetermined size from each of the plurality of images obtained by the camera, and a panoramic image generation unit which defines predetermined energy based on the plurality of feature regions included in each of the plurality of images, associates the plurality of feature regions between the plurality of images such that the energy is minimized, and generates a panoramic image of the inside of the object based on the association result.

By solving an energy minimization problem, it is possible to generate panoramic images without estimating the camera motion. As a result, when the estimation of the camera motion is erroneous, the problem that the video mosaicking process does not succeed is eliminated so that accurate panoramic images can be obtained, which makes it possible to prevent the physician's erroneous diagnosis.

The predetermined energy may be determined based on the differences in pixel value between the plurality of feature regions included in each of two temporally successive images.

In addition, the predetermined energy may be determined based on the differences in area between triangular patches obtained by connecting the plurality of feature regions included in each of two temporally successive images.

Further, the camera may be an omnidirectional camera, and the predetermined energy may be determined based on a difference between (i) a coordinate obtained by correcting, based on a movement component of the omnidirectional camera, a coordinate of a great circle which appears in an image after a first image taken by the omnidirectional camera is transformed in a spherical coordinate system with its center at a viewpoint of the omnidirectional camera, and (ii) a coordinate of a great circle which appears in an image after a second image temporally successive to the first image and taken by the omnidirectional camera is transformed in the spherical coordinate system.

Furthermore, the predetermined energy may be determined based on the degree of deviation of a plurality of control points, in a second image taken by the camera, which respectively correspond to a plurality of control points selected from a first image taken by the camera.

In addition, the predetermined energy may be determined based on the degree of deviation between a plurality of control points selected from a first image taken by the camera and a plurality of control points, in a second image taken by the camera, which respectively correspond to the plurality of control points selected from the first image.

In addition, the plurality of feature regions may be regions, among the plurality of regions having a predetermined size included in each of the images, in which the squared sum of derivatives of pixel values is greater than a predetermined threshold value.

By selecting the feature regions in a manner as described above, regions in which variations in luminance are small are not to be extracted as feature regions of the object. As a result, it is possible to accurately associate feature regions between images, and obtain accurate panoramic images. Thus, it is made possible to prevent the physician's erroneous diagnosis.

More preferably, the camera is an omnidirectional camera, and the image generation unit generates a panoramic image having a fixed visual angle with respect to the direction perpendicular to the traveling direction of the omnidirectional camera by performing a video mosaicking process on the plurality of images obtained by the omnidirectional camera.

In this structure, an omnidirectional camera is provided to the endoscope. The omnidirectional camera is capable of observing the field of view lateral to the traveling direction of the endoscope. Therefore, it is possible to visually recognize lateral directions of the digestive organs, which is hard for conventional probe-type endoscopes. Simultaneously, it is also possible to acquire seamless 360-degree circumferential video. As a result, it is made possible to prevent the physician from overlooking any nidus.

In addition, the omnidirectional camera has a sufficient view angle for the lateral field of view, and therefore taken video images include not only images of the inner walls of the digestive organs that are seen in front of the side surface, but also images taken at a given visual angle. In addition, the video taking involves movement of the camera, and therefore an enormous amount of images are obtained. Among them, images of the front of intestinal walls and images of the back of the intestinal walls are included. Therefore, by viewing these images, dead area portions to the physician are reduced, which makes it possible to prevent any lesion from being overlooked.

In addition, the camera may be mounted on the tip of a probe that is to be inserted into the digestive organs, and the camera may be enclosed in a capsule that can be swallowed by a human or an animal.

EFFECTS OF THE INVENTION

As described above, according to the present invention, it is possible to provide an endoscope and an endoscope system that are free from a dead area and capable of preventing the physician from overlooking any nidus.

In addition, it is possible to provide an endoscope and an endoscope system that improve the physician's diagnosis efficiency.

Thus, it is possible to obtain panoramic images of side surfaces inside the digestive organs, including side surfaces in the forward direction and side surfaces in the backward direction, images of which are conventionally difficult to take, resulting in extremely significant contributions to preventing the physician from overlooking any lesion and the improvement of diagnosis efficiency and immeasurable contributions to the field of medical instruments and the progress of medical science.

BRIEF DESCRIPTION OF DRAWINGS

FIG. 16 is a flowchart illustrating an image pasting process taking the motion of the small intestine into consideration.

FIGS. 17A and 17B are each a diagram illustrating exemplary triangular patches, in which FIG. 17A shows triangular patches in an f-th frame and FIG. 17B shows triangular patches in a (f+1)-th frame.

NUMERICAL REFERENCES

Figure 1:
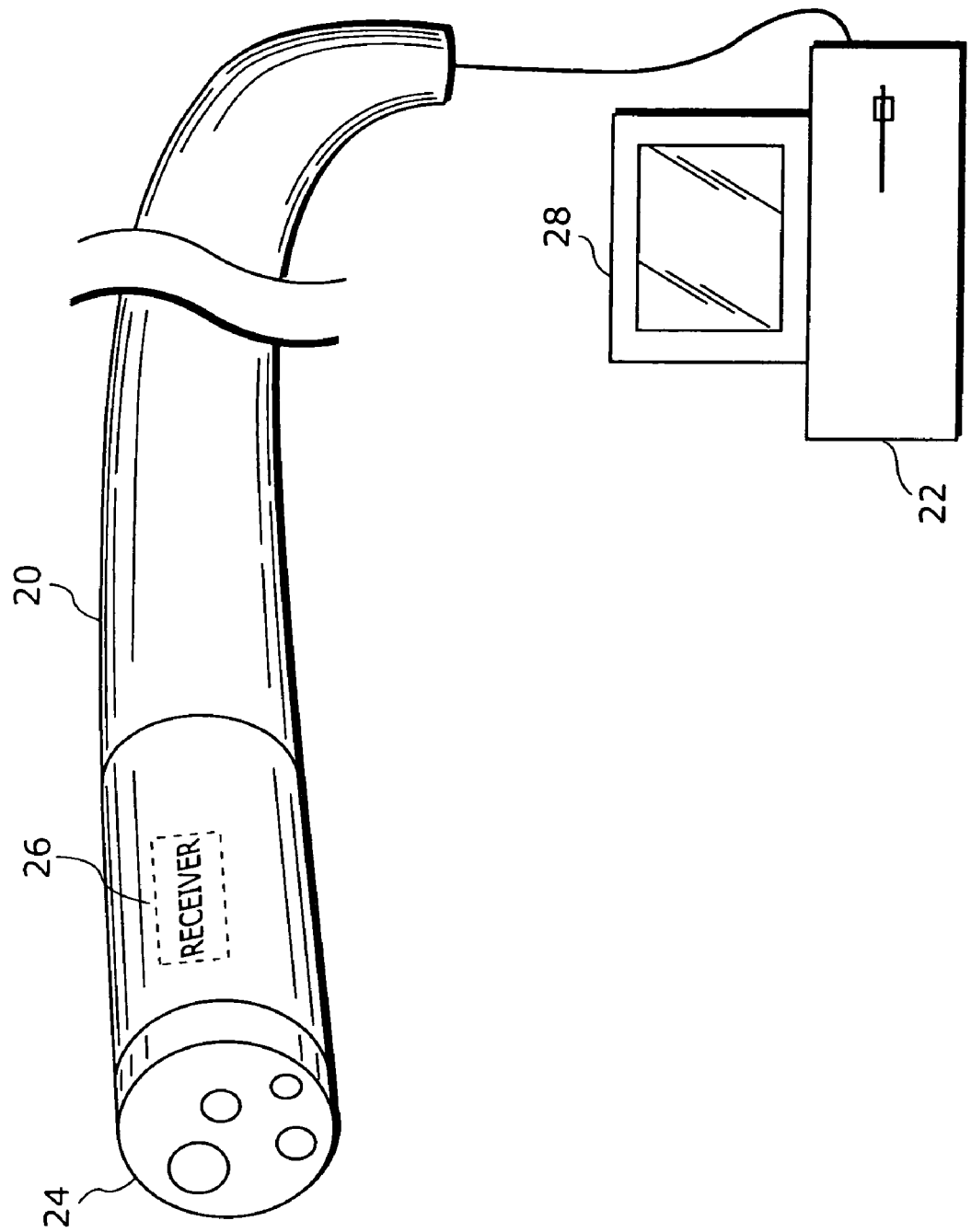
FIG. 1 is a diagram illustrating the configuration of a probe-type endoscope according to first and second embodiments of the present invention.

20 Probe-type endoscope
22 Image processing device
24 Tip portion
26 Receiver
28 Display unit
32 Omnidirectional camera
34 Light
36 Forceps
38 Rinse water injection port
42 Hyperboloidal mirror
44 Imaging unit
46 Lens
48 Imaging surface
50 Capsule endoscope
60 Small intestine

BEST MODE FOR CARRYING OUT THE INVENTION

Hereinafter, endoscope systems according to embodiments of the present invention will be described with reference to the drawings.

First Embodiment

Configuration of Endoscopes

The configuration of endoscopes according to the present embodiment is described with respect to two types of endoscopes: a probe-type endoscope and a capsule endoscope.

1. The Probe-Type Endoscope

Figure 2:
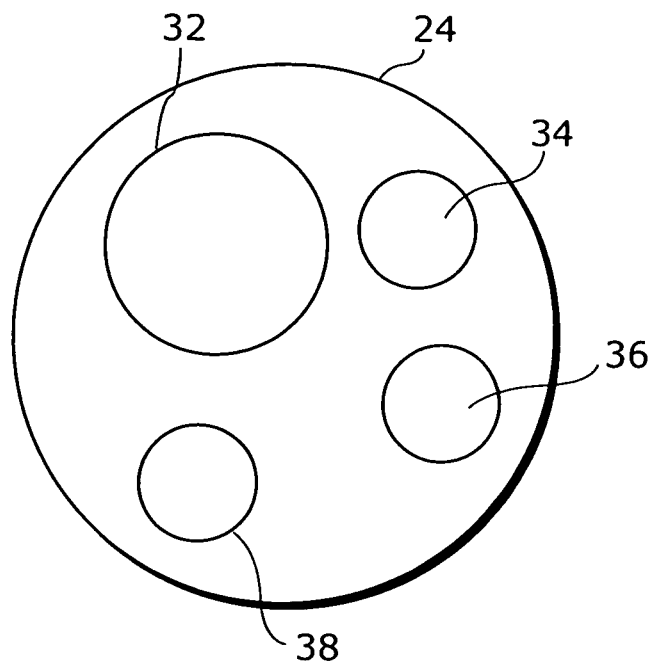
FIG. 2 is an external view of a tip portion of the probe-type endoscope shown in FIG. 1.

FIG. 1 is a diagram illustrating the configuration of a probe-type endoscope according to the first embodiment of the present invention. FIG. 2 is an external view of a tip portion 24 of the probe-type endoscope 20 shown in FIG. 1. The tip portion 24 of the probe-type endoscope 20 is provided with an omnidirectional camera 32, a light 34, a forceps 36 and a rinse water injection port 38.

The omnidirectional camera 32 is a device for taking images the inside of digestive organs, and is able to take 360-degree images of its surroundings. The light 34 is used for lighting up the inside of the digestive organs. The forceps 36 is a tool used for pinching and pressing tissues and nidi inside the digestive organs. The rinse water injection port 38 is an injection port of water for rinsing the omnidirectional camera 32 having adhered thereto secretions inside the digestive organs.

The probe-type endoscope 20 is provided with a receiver 26 composed of orthogonal coils, and the receiver 26 is used for estimating the position and attitude of the probe-type endoscope 20.

An image taken by the omnidirectional camera 32 is presented on a display unit 28 of an image processing device 22 connected to the probe-type endoscope 20.

Figure 3:
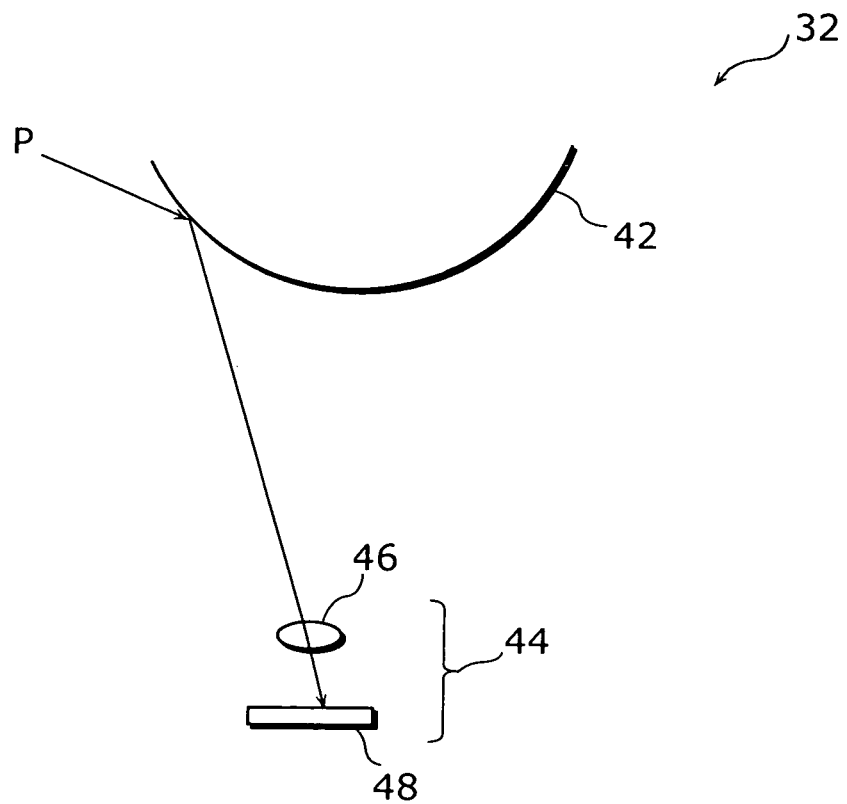
FIG. 3 is a diagram showing the internal structure of an omnidirectional camera.

FIG. 3 is a diagram showing the internal structure of the omnidirectional camera 32. The omnidirectional camera 32 is provided with a hyperboloidal mirror 42 and an imaging unit 44. The hyperboloidal mirror 42 is a mirror in the form of one of two sheets of a two-sheeted hyperboloid. The imaging unit 44 includes a lens 46 for receiving light reflected by the hyperboloidal mirror 42, and an imaging surface 48. Note that the lens 46 has the lens center at the focal position of the other sheet of the two-sheeted hyperboloid.

It is assumed that HyperOmni Vision proposed by Yamazawa et al. is used as the omnidirectional camera 32 using the hyperboloidal mirror 42.

Figure 4:
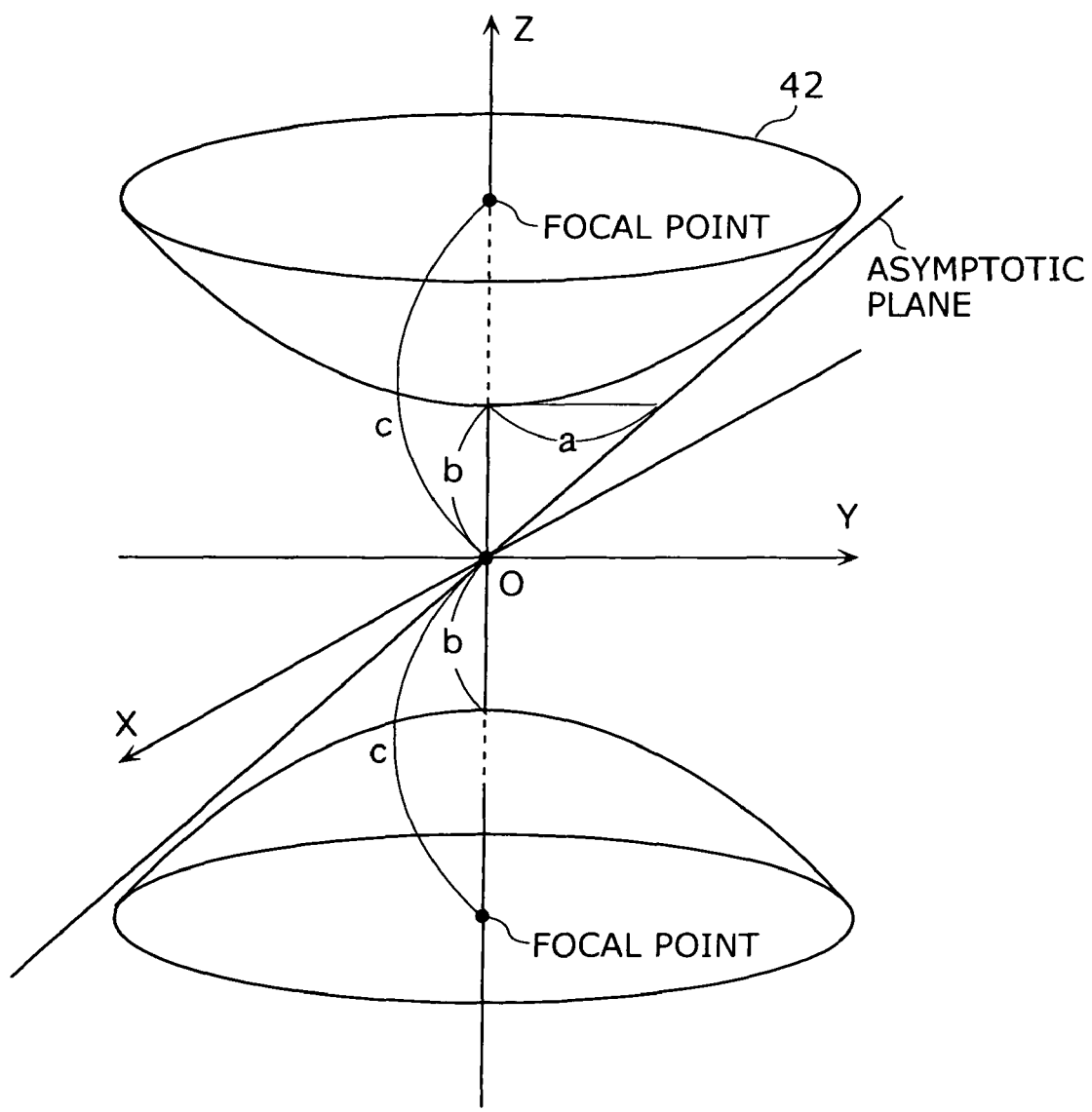
FIG. 4 is a diagram for explaining a two-sheeted hyperboloid.

Referring to FIG. 4, the hyperboloidal mirror 42 uses as a mirror the sheet of the two-sheeted hyperboloid that is located in the region where Z>0. The two-sheeted hyperboloid is a curved surface obtained by rotating a hyperbolic curve about the real axis (Z-axis). The two-sheeted hyperboloid has two focal points (0,0,+c) and (0,0,−c). Where

[Expression 1]

$$c = \sqrt{a^2 + b^2}.$$

Figure 5:
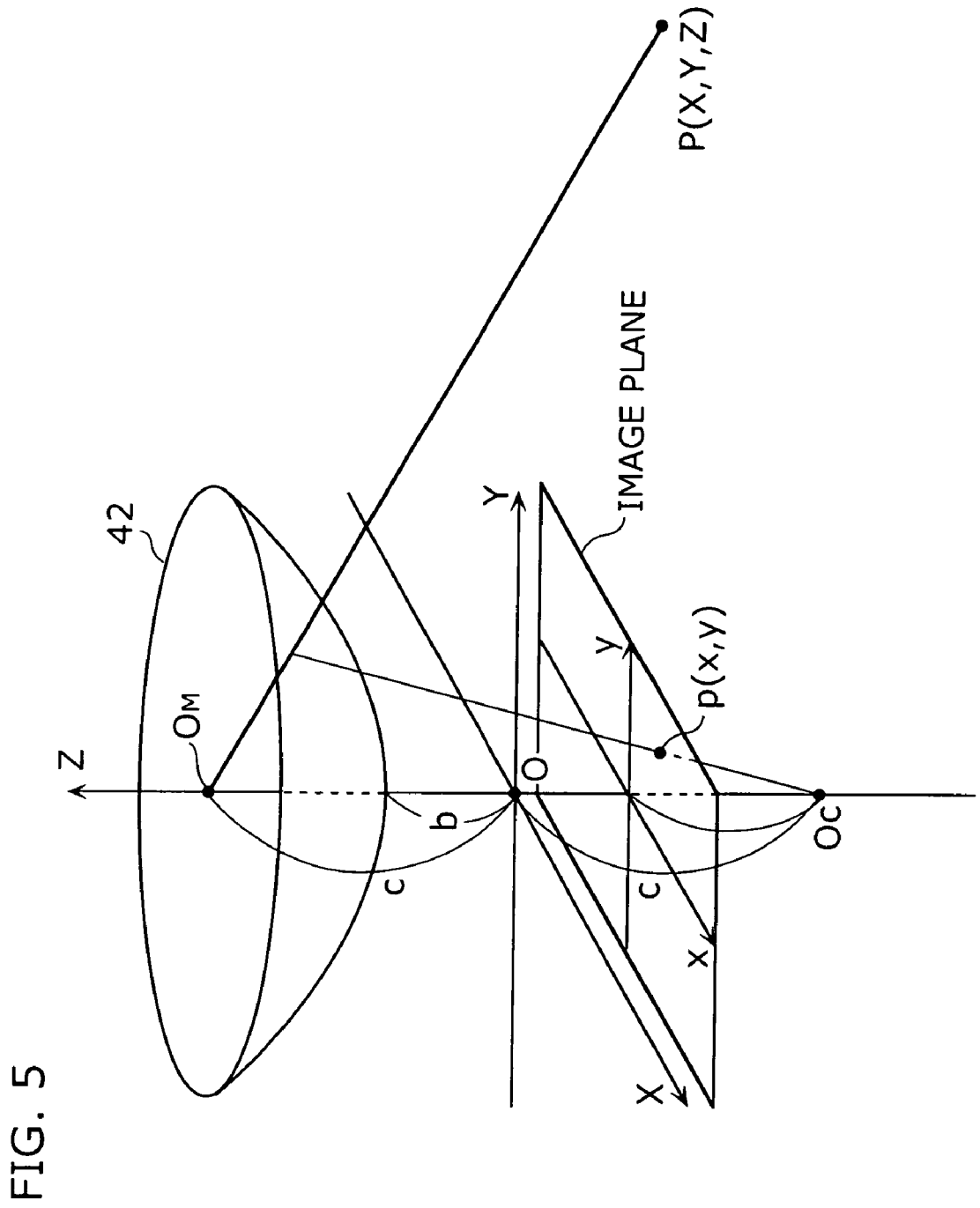
FIG. 5 is a diagram illustrating the configuration of an omnidirectional camera.

Here, consider a three-dimensional coordinate system O-XYZ having the Z-axis as the vertical axis as shown in FIG. 5. In this case, the two-sheeted hyperboloid is expressed by the following equation (1).

[Expression 2]

$$\frac{X^2 + Y^2}{a^2} - \frac{Z^2}{b^2} = -1 \qquad (1)$$

Figure 6:
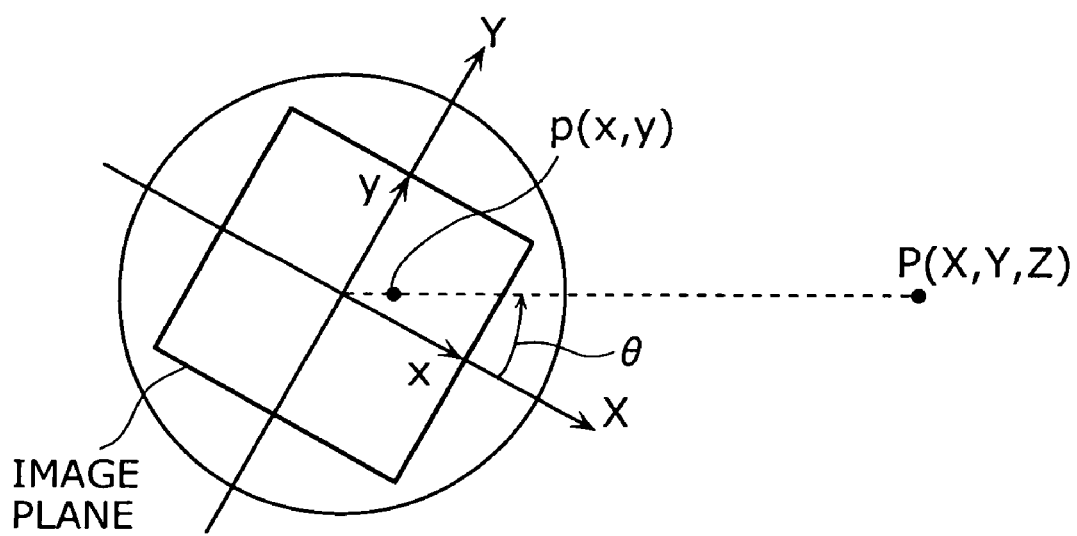
FIG. 6 is the first diagram for explaining the relationship between an arbitrary point in space and a mapping point on an image.

Note that constants a and b define the shape of a hyperbolic curve. Referring to FIG. 6, the omnidirectional camera HyperOmni Vision is composed of the hyperboloidal mirror 42, which is provided in the region where Z>0 so as to face downward in the vertical direction, and an imaging unit (not shown), which is provided therebelow so as to face upward in the vertical direction. In this case, the hyperboloidal mirror 42 and the imaging unit are positioned such that the focal point OM of the hyperboloidal mirror 42 and the lens center OC of the camera are located at two focal points (0,0,+c) and (0,0,−c), respectively, of the two-sheeted hyperboloid. The image plane xy is assumed to be a plane parallel to the XY plane and distanced by a focal distance f of the camera from the lens center OC of the imaging unit. The reflection surface of the hyperboloidal mirror 42, the focal point OM of the hyperboloidal mirror 42 and the lens center OC of the camera are expressed by the following equation (2).

[Expression 3]

$$\begin{cases} \text{Mirror surface} & \frac{X^2+Y^2}{a^2}-\frac{Z^2}{b^2}=-1(Z>0) \\ \text{Focal point } OM \text{ of the mirror} & (0,0,+c) \\ \text{Less center } OC \text{ of the camera} & (0,0,-c) \end{cases} \quad (2)$$

Referring to FIG. 6, when a mapping point on an image that corresponds to an arbitrary point P(X,Y,Z) in space is taken as p(x,y), the azimuth angle θ at the point P is expressed by the following equation (3).

$$\tan\theta = Y/X = y/x \quad (3)$$

Specifically, the azimuth angle θ at the point P defined by Y/X is obtained by calculating the azimuth angle θ at the mapping point p defined by y/x. In this manner, the azimuth angle θ of a target object within a 360-degree panoramic region directly appears as the map azimuth of the object on the image plane.

Figure 7:
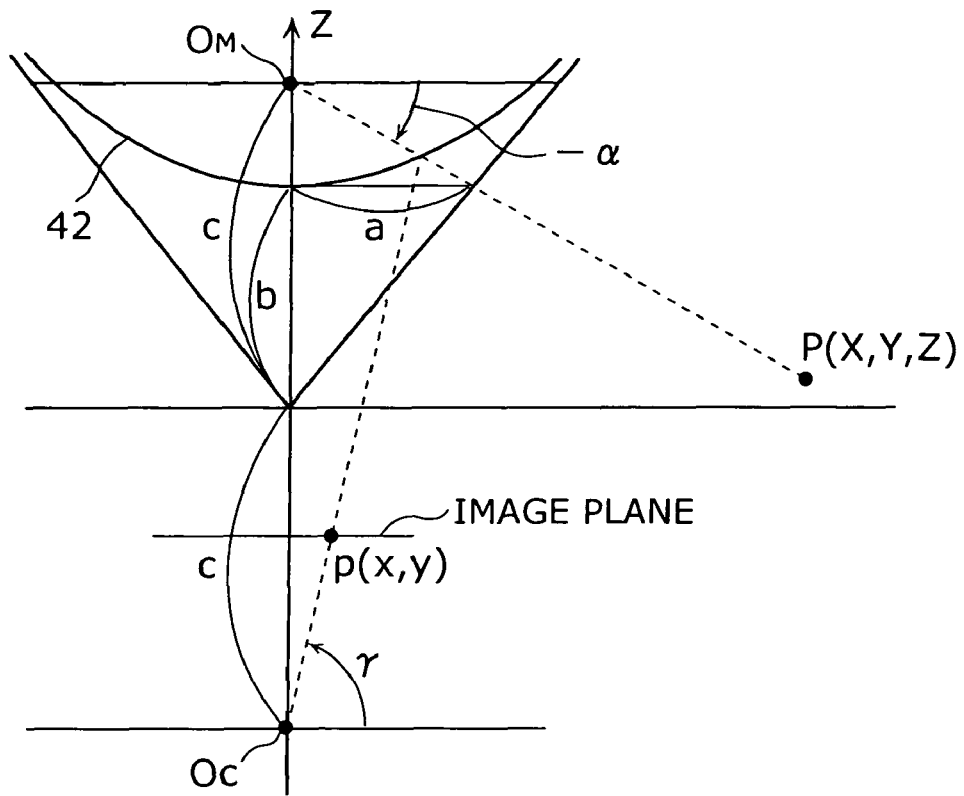
FIG. 7 is the second diagram for explaining the relationship between an arbitrary point in space and a mapping point on an image.

Referring to FIG. 7, supposing a vertical section including the point P and the Z-axis, the relationship of the following equation (4) is established between the point P and the mapping point p.

[Expression 4]

$$\begin{cases} Z = \sqrt{X^2+Y^2}\tan\alpha + c \\ \alpha = \tan^{-1}\frac{(b^2+c^2)\sin\gamma - 2bc}{(b^2+c^2)\cos\gamma} \\ \gamma = \tan^{-1}\frac{f}{\sqrt{x^2+y^2}} \end{cases} \quad (4)$$

Specifically, the azimuth angle θ and the depression angle α at the point P from the focal point OM of the hyperboloidal mirror 42 is uniquely obtained based on the mapping point p(x,y) by providing the lens center OC of the camera at the focal position of the hyperboloid. In this case, the focal point OM of the hyperboloidal mirror 42 is fixed, and therefore an input image can be transformed to an image (a panoramic image) viewed from the focal point OM of the hyperboloidal mirror 42, which is obtained by rotating the camera about the vertical axis, or a normal camera image.

The omnidirectional camera HyperOmni Vision is disclosed in detail in "Kazumasa Yamazawa et al., 'Omnidirectional Visual Sensors for Navigation of Mobile Robots', Journal of the Institute of Electronics, Information and Communication Engineers, D-II, Vol. J79-D-II, No. 5, pp. 698-707 (May, 1996)", etc.

2. The Capsule Endoscope

Figure 8:
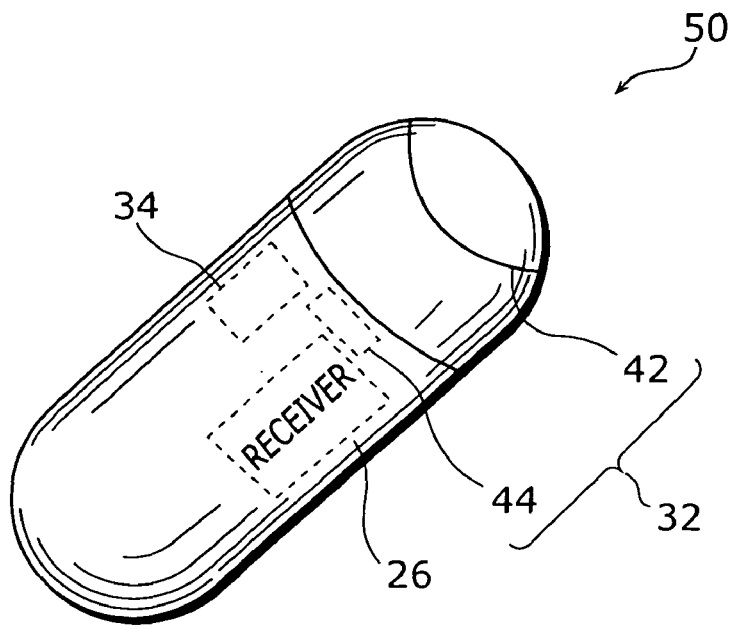
FIG. 8 is a diagram illustrating the configuration of a capsule endoscope.

FIG. 8 is a diagram illustrating the configuration of a capsule endoscope. The capsule endoscope 50 is provided with an omnidirectional camera composed of a hyperboloidal mirror 42 and an imaging unit 44, a light 34 and a receiver 26. An image taken by the imaging unit 44 is delivered to an externally provided image processing device, and the image processing device processes and presents the image.

[Generation of Digestive Organ Spread Images]

The omnidirectional camera 32 attached to an endoscope (a probe-type endoscope or a capsule-type endoscope) as configured above is used to obtain a video. In particular, the capsule endoscope 50 acquires a 360-degree video around the endoscope by the encapsulatable omnidirectional camera 32.

The range of video obtainable from one frame of endoscope video is narrow, but by reconstructing the movement of the endoscope, it is possible to superimpose frames from the video on one another.

Figures 9A, 9B, 9C, 9D:
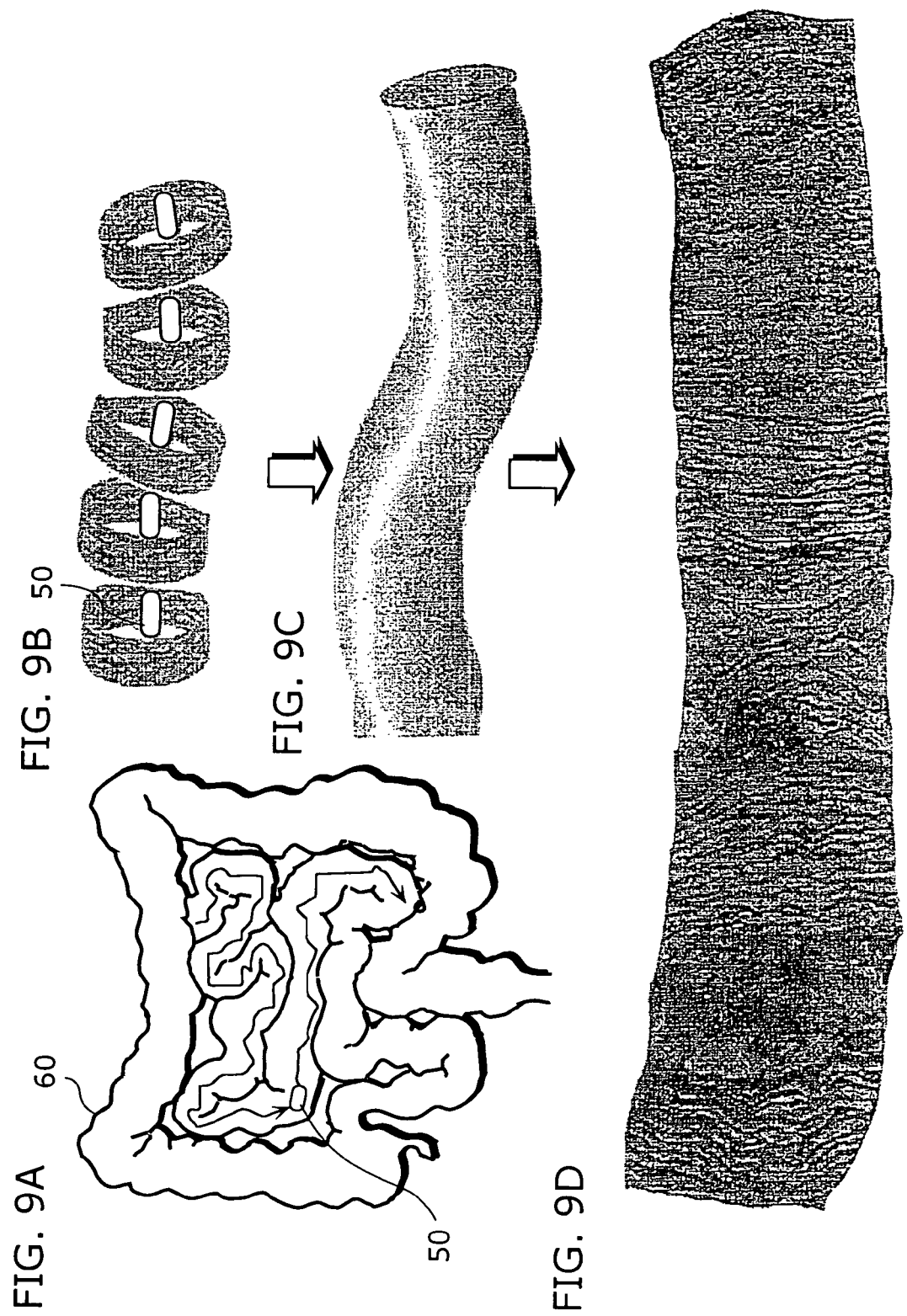
FIGS. 9A to 9D are illustrations for explaining image processing by a mosaicking process.

FIG. 9A to 9D are each a conceptual diagram for explaining the details of image processing. FIG. 9A is an illustration showing how the capsule endoscope 50 moves within a small intestine 60. As indicated by the arrows in the illustration, the capsule endoscope 50 travels through the small intestine 60 from the oral cavity side to the anus side in accordance with segmentation and peristalsis movements of the small intestine 60. The segmentation movement refers to motion caused by adjacent circular muscles in the small intestine 60 intermittently contracting at the same time. In addition, the peristalsis movement refers to motion for moving food forward, which is caused by a combination of circular muscles and longitudinal muscles.

Because the capsule endoscope 50 spends about eight hours to pass through the digestive organs, the traveling speed is slow. Accordingly, images between frames considerably overlap each other, so that it is possible to densely paste the images.

Therefore, images obtained by the omnidirectional camera are transformed to a panoramic image as in FIG. 9B, and the shape of a digestive organ is modeled into a simple geometric shape on which the image is pasted as in FIG. 9C. Thereafter, by generating a spread image of the digestive organ, which is partially dissected, as shown in FIG. 9D, it is possible to obtain a virtual anatomic image of the digestive organ. As a result, the physician is able to quickly find any nidus by viewing the anatomic image, which can be considerable support to the diagnosis. For that purpose, it is a significant problem to accurately detect movement components of the camera.

[Motion Estimation of the Omnidirectional Camera and Image Generation]

The motion of the omnidirectional camera 32 can be detected from corresponding image points in a sequence of temporally successive images. In the omnidirectional camera 32, corresponding points are projected onto the imaging surface 48 as azimuths. Therefore, an image can be represented using a spherical coordinate system.

Figure 10:
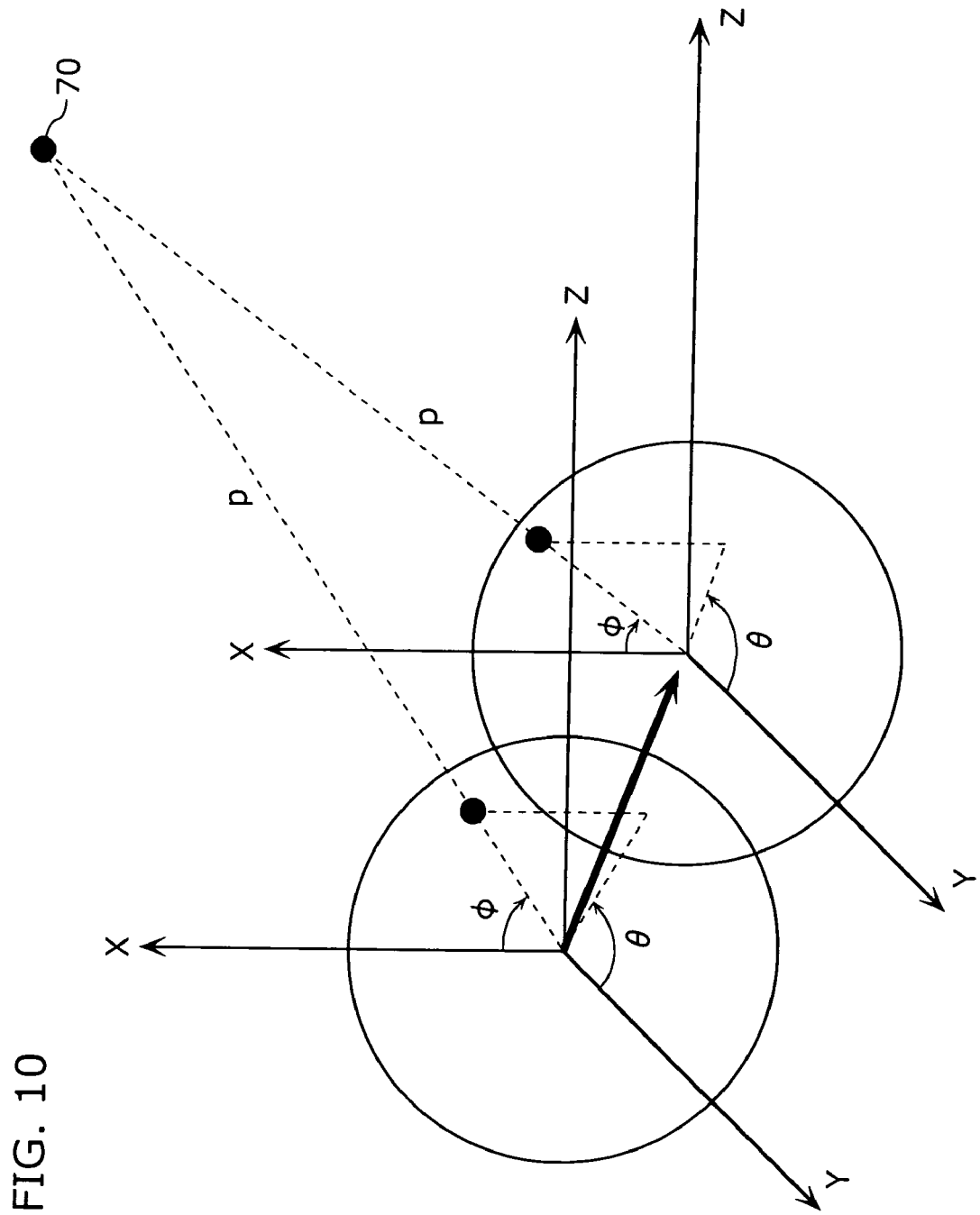
FIG. 10 is a diagram illustrating the movement of an omnidirectional camera in a spherical coordinate system.

FIG. 10 is a diagram illustrating the movement of the omnidirectional camera 32 in a spherical coordinate system. In FIG. 10, the movement of the omnidirectional camera 32 is represented as the movement of the coordinate system, and the same corresponding point at the position of the omnidirectional camera 32 before and after the movement is indicated by a corresponding point 70 in the diagram. Note that the position of the omnidirectional camera 32 is the origin of the coordinate system.

The relationship between the spherical coordinate system and the XYZ-coordinate system is indicated by the following equation (5).

[Expression 5]

$$X = \rho \sin \phi \cos \theta$$

$$Y = \rho \sin \phi \cos \theta$$

$$Z = \rho \cos \theta \quad (5)$$

In the spherical coordinate system, a three-dimensional coordinate point $(\rho, \Phi, \Theta)$ on the imaging surface $(\rho_0, \phi, \theta)$ is projected at the imaging surface in accordance with the following equation (6).

[Expression 6]

$$\phi' = \Phi'$$

$$\theta' = \Theta \quad (6)$$

In addition, the relationship between the coordinate system after the camera has been moved and the coordinate system before the movement can be represented by a rotating matrix R and a translation matrix t, and the relationship indicated by the following equation (7) is established.

[Expression 7]

$$\begin{pmatrix} \rho' \\ \Phi' \\ \Theta' \end{pmatrix} = R \begin{pmatrix} \rho \\ \Phi \\ \Theta \end{pmatrix} + t \quad (7)$$

$$R = \begin{pmatrix} r_{11} & r_{12} & r_{13} \\ r_{21} & r_{22} & r_{23} \\ r_{31} & r_{32} & r_{33} \end{pmatrix}, t = \begin{pmatrix} \rho_t \\ \Phi_t \\ \Theta_t \end{pmatrix}$$

When the distance from the camera to a target point is approximated to a constant value $\rho_0$, by substituting the equation (7) into the equation (6), the relationship of the following equation (8) is established to obtain a rotational parameter and a translational parameter from a plurality of fixed three-dimensional coordinate points.

[Expression 8]

$$\phi' = r_{21}\rho_c + r_{22}\phi + r_{23}\theta + \phi_1$$

$$\theta' = r_{31}\rho_c + r_{32}\phi + r_{33}\theta + \theta_1$$

However, the inner wall of a digestive organ performs the segmentation movement, and therefore its video exhibits a slow movement. In an image sequence employed for mosaicking, however, the movement is restricted to be extremely slight, and therefore it is possible to linearly approximate the moving speed of the three-dimensional target object between several successive frames. Accordingly, the camera motion parameters are determined such that the amount of displacement Di in the case where the camera motion that is determined at an image taking time $t_i$ based on an immediately previous image taking time $t_{i-1}$ is projected onto the plane of projection is maintained at an immediately subsequent image taking time $t_{i+1}$. The amount of displacement $D_i$ is measured hourly, so as to obtain linearly approximated camera motion parameters in a short period of time and nonlinear camera motion parameters in a long period of time.

Figure 11:
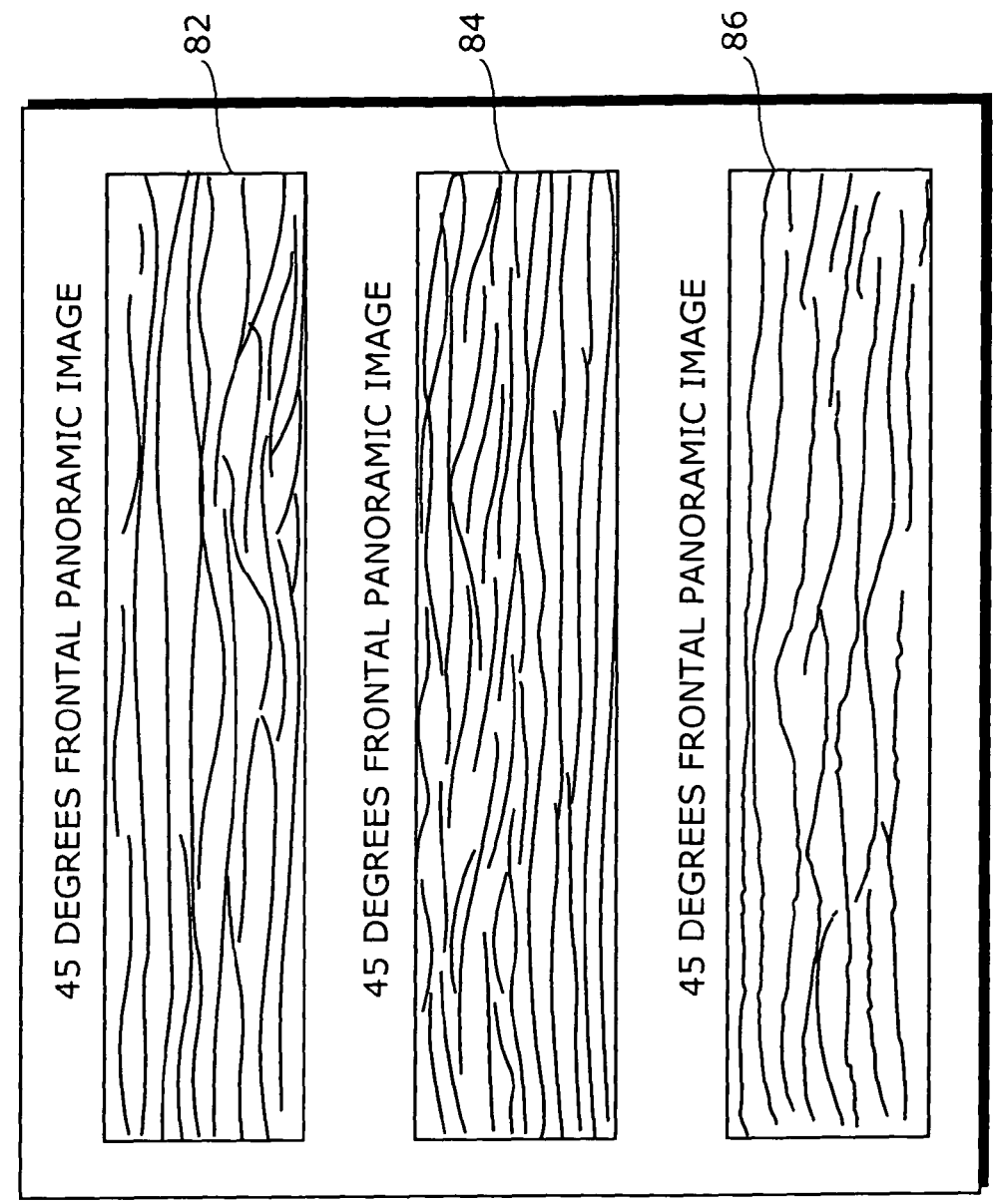
FIG. 11 is an illustration showing exemplary images of different viewable angles.

When the camera motion is determined, the digestive organ is then modeled to a cylinder or the like, which represents the outline of its shape, and an image is projected onto the cylindrical surface. At this time, the image is generated such that its viewable angle varies depending on images that are to be pasted. FIG. 11 is an illustration showing exemplary images of different viewable angles. As shown in FIG. 11, an image is generated so as to simultaneously present a 360-degree panoramic surrounding image of the inside of the digestive organ 45 degrees ahead of the endoscope, a panoramic image lateral to the endoscope and a panoramic image for 45 degrees behind the endoscope.

Figure 12:
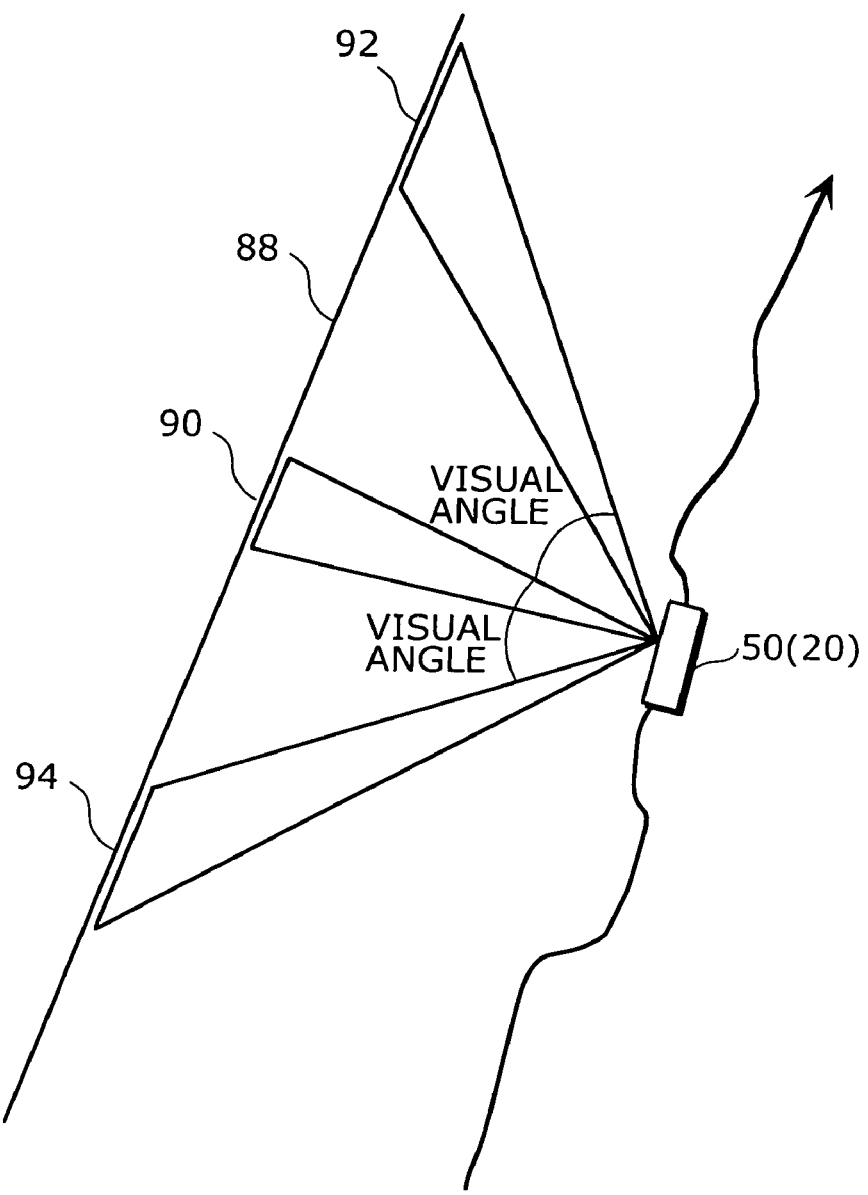
FIG. 12 is a diagram for explaining a method for generating a panoramic image.

FIG. 12 is a diagram for explaining a method for generating a panoramic image. First, based on images taken by the omnidirectional camera 32 of the endoscope 50 (20), a panoramic image 84 of a side surface 90 of the inner wall taken by the omnidirectional camera 32 from the front is generated. In this case, the average of several tens of seconds of camera motions is taken as a reference attitude of the camera, and the panoramic image 84 of the side surface taken from that attitude is obtained by performing a video mosaicking process based on a plurality of images spanning several tens of seconds. This operation is applied to all camera motions to generate the panoramic image 84 of the inner wall of the digestive organ viewed from the front in the lateral direction.

Next, a panoramic image in which plicae of the digestive organ are readily observed is generated. When the image is composed of images at a forward visual angle, e.g., 45 degrees, from the side of the endoscope 50 (20) in the reference attitude, a plurality of images are pasted by a video mosaicking process to generate a panoramic image 82 of an inner wall 92 of the digestive organ positioned in the forward direction and viewed from the side of the endoscope. Similarly, a panoramic image 86 of an inner wall 94 of the digestive organ positioned in the backward direction and viewed from the side of the endoscope is generated.

Described next is a technique for generating an image of an inner wall seen from an arbitrary angle based on video of a moving digestive organ taken by the omnidirectional camera, by estimating not only the motion of the camera but also three-dimension information of the digestive organ.

Conventionally, in the problem of estimating the motion of the camera, an observation target is assumed to be standing still, but it is hard to assume that the observation target is standing still because the segmentation movement occurs in video of the inside of intestines. However, the movement is at an extremely slow speed, and therefore the motion of the camera can be estimated by a two-stage approach as below.

(1) The camera motion is estimated from two successive images in a video picture by using an epipolar constraint condition. The two images are taken at an extremely short interval, and therefore it is assumed that the observation target is standing still during that period.

(2) A number of chronologically obtained images are used to correct the motion of the camera that is obtained by the method of (1), based on a bundle adjustment technique. There is a difference in time of acquisition between the images, and therefore the segmentation movement occurs during that period. Accordingly, the camera motion is estimated with the term of time variation added at the position of a feature point that is being tracked.

First, in the method of (1), a feature point is extracted from an image, and the feature point is tracked between successive images. Since the technique for performing them has been proposed in various forms, such an approach is used. For example, methods described in "C. Harris and M. Stephens, 'A combined corner and edge detector', In Proc. Fourth Alvey Vision Conference, pp. 147-151, 1988", "B. Lucas and T. Kanade, 'An Iterative Image Registration Technique with an Application to Stereo Vision', Proc. of 7th International Joint Conference on Artificial Intelligence (IJCAI), pp. 674-679", etc., are known.

Specifically, here, the camera motion is estimated similarly to these approaches. Corresponding feature points m and m' in two images obtained from different viewpoints establish a relationship such as mEm'=0 when a fundamental matrix E is used based on the epipolar constraint. Here, when seven or more pairs of feature points are obtained, it is possible to determine the fundamental matrix E, and the fundamental matrix E can be decomposed into a rotating matrix R and a translation vector t of a coordinate system. Thus, it is possible to estimate the camera motion. Note that the association between the feature points contains error, and therefore any erroneous association is eliminated using a RANSAC (Random Sample Consensus) algorithm, which is an approach for robust estimation. When the camera motion is found, it is possible to calculate positions of the feature points in three-dimensional space based on the principle of trigonometrical surveying. When an intestine is observed, feature points are arranged in the form of a cylinder. Therefore, a cylindrical model is fitted to the calculated positions of the feature points to estimate the center $v_c$ and axial direction $v_a$ of the cylinder. They are calculated using the least squares method.

Next, in the method of (2), the camera position and the positions of the feature points, which are obtained by the above-described method, are corrected using a number of images. In this method, an error represented by the following equation (9) is minimized. Here, $M_i$ is the position of a feature point in three-dimensional space, and $m_{ij}$ is the position of a feature point corresponding to $M_i$ in the image of image number j. $R_j$ and $t_j$ represent the position and attitude of the camera in the image number j. In the bundle adjustment, parameters are taken as $M_i$, $R_j$ and $t_j$ to minimize the error. For minimization, iterative calculation such as the Levenberg-Marquardt method is used.

However, because in the video of the inside of the intestine, the position $M_i$ in the three dimensions moves due to the segmentation movement during observation, the above error is corrected and an error represented by the following equation (10) is minimized. Here, a function f is a model that represents the segmentation movement. As described above, the segmentation movement occurs because of adjacent circular muscles intermittently contracting at the same time. Because the circular muscles are arranged at regular intervals, it is possible to approximate changes of the inner wall of the digestive organ to a sine wave; the function f is represented as in the following equation (11).

[Expression 9]

$$\sum_{j}^{K}\sum_{i}^{N}|P(R_jM_i+t_j)-m_{ij}|^2 \quad (9)$$

$$\sum_{j}^{K}\sum_{i}^{N}|P(R_jf(M_i,j)+t_j)-m_{ij}|^2 \quad (10)$$

-continued $$f(M,j) = M + a\sin(bj-cv)v_n \quad (11)$$
$$v = (M-v_c)\cdot v_a$$
$$v_n = M - v_c - v$$

Here, $v_c$ and $v_a$ are the center position and axial direction of the above-described cylindrical model. The function f is represented by parameters a, b and c, and therefore a, b and c are added to the parameters used for the bundle adjustment to minimize the error.

In addition, there is a method that uses the result of acquiring camera movement components for generating a panoramic image, by means of a sensor attached to the endoscope as well as based on images. Real-time estimation of six degrees of freedom for the position and attitude of a sensor by using magnetic field, microwave or the like exists as a commercially available technique. Although it is possible to generate a panoramic image based on the three-dimensional position/attitude information obtained by the sensor, estimation accuracy of such sensor, in the case of a magnetic sensor, is normally 0.5 degrees for bearing accuracy and about 1.8 mm for positional accuracy, and therefore if the information is used as it is, the camera motion is inaccurate. Thus, it is difficult to generate an accurate panoramic image. Accordingly, the three-dimensional position/attitude information obtained by the sensor is taken as an initial value for the above-described method for estimating the camera motion, thereby making it possible to generate images at higher speed.

Note that there are magnetic sensors for estimating the position and attitude as follows.

An endoscope position detecting unit "UPD" (trademark of Olympus Corp.) distributed by Olympus Corp. is capable of measuring the entire geometry of the endoscope by a magnetic sensor.

Additionally, in general, typical positional measurement approaches using a magnetic sensor utilizes the fact that when a receiver (orthogonal coils) attached to an endoscope tip portion is placed in a magnetic field of a transmitter (orthogonal coils) to which alternating current is being applied, an electromotive current is induced in the receiver, and calculates the position and azimuth of the receiver with respect to the transmitter as a base point based on the magnitude of the electromotive current. For example, FASTRACK (registered trademark of Polhemus Inc.) by Polhemus Inc. is capable of measuring six degrees of freedom: three-dimensional coordinate values (X, Y, Z) and Eulerian angles (Pitch, Yaw, Roll).

In addition, a magnetic sensor "miniBIRD" (registered trademark of Ascension Technology Corporation), which utilizes a direct current magnetic field, is a compact sensor of 10 mm×5 mm×5 mm, which can be attached to the tip of a medical instrument to measure six-degree-of-freedom values (three-dimensional coordinate values and Eulerian angles) in real time. Further, similar to the magnetic sensor, it is possible to provide an initial value for panorama generation by utilizing an approach that utilizes a delay in arrival time of radio waves such as microwaves to an antenna to estimate the three-dimensional position of the emission source.

As described above, according to the present embodiment, by using an omnidirectional camera for a probe-type endoscope, it is made possible to readily realize an omnidirectional endoscope, which achieves better viewability than existing endoscopes. Specifically, it is possible to readily realize lateral viewing, which is hard for conventional probe-type endoscopes.

In addition, it is possible to present to the physician a panoramic image taking account of a visual angle. Thus, it is possible to present to the physician an image in the backward direction from the side, which is hard for conventional probe-type endoscopes. In particular, it is often the case that a lower endoscope observes large plicae of the rectum and the large intestine, and the back sides of plicae in a portion of the large intestine that is greatly curved cannot be viewed with any existing endoscope, which results in a risk of overlooking any nidus; however it is highly probable that the omnidirectional endoscope leads to the avoidance of such risk.

Further, because the capsule endoscope, which will be put into a practical use in the near future, moves through digestive organs as in the flow of food, it is difficult to control its direction and position, and in some cases, a video of the surrounding area cannot be taken only in the current forward field of view. On the other hand, a capsule endoscope provided with an omnidirectional camera has a full-circumferential, lateral field of view and covers a wide range, and therefore there is a low possibility of leaving an uncaptured portion. Additionally, in order to efficiently examine a large amount of image data taken by the camera, a highly skilled technique is required. An image obtained by spreading a panoramic picture into which a large amount of images are pasted allows even a gastroenterologist who is not skilled with the endoscope to readily carry out diagnosis, which serves for improvement of medical technology.

Furthermore, the estimation of camera motion from images normally provides accuracy suitable for panorama generation, but when the position or attitude of the endoscope is abruptly changed, erroneous estimation may occur. Therefore, in the present invention, by additionally using a position/attitude sensor such as a magnetic sensor, it is possible to previously measure the approximate position and attitude with the position/attitude sensor and, thereafter, to estimate the position and attitude in detail by image processing. Thus, it is possible for the sensor to prevent considerably erroneous estimation, making it is possible to generate a panoramic image with high accuracy as well as to generate a panoramic image at high speed.

In addition, as shown in the equation (11), when correcting the camera motion, the changes of the inner wall of the digestive organ due to the segmentation movement are approximated to a sine wave. Therefore, it is possible to obtain more accurate camera motion. Moreover, it is possible to carry out accurate generation of a panoramic image.

Second Embodiment

Described next is the configuration of an endoscope according to a second embodiment of the present invention. The configuration of the endoscope according to the second embodiment is similar to that of the probe-type endoscope or the capsule endoscope according to the embodiment. However, it differs from the first embodiment in the following three points.

(1) In the first embodiment, the motion estimation of the omnidirectional camera 32 is carried out by detection from corresponding image points in a sequence of temporally successive images, whereas in the second embodiment, feature regions in images are obtained to associate the regions.

(2) Additionally, in the first embodiment, the segmentation movement of the inner wall of a digestive organ is formulated to correct the camera motion, whereas in the second embodiment, in addition to that, the peristalsis movement of the inner wall of the digestive organ is also formulated.

(3) Further, in the first embodiment, after the motion estimation of the camera is carried out by obtaining corresponding points between temporally successive images, a process of generating a panoramic image by pasting the images is performed, whereas in the present embodiment, an energy minimization problem is applied to simultaneously perform the motion estimation of the camera and the generation of a panoramic image.

These are described in detail below.

[(1) Regarding the Association Between Regions]

In order to address the case where it is not possible to detect a clear feature point in an image inputted from the camera as in the case of the inner wall of a digestive organ, the image is divided into blocks of small regions (8×8 or 16×16 pixels) to evaluate internal texture components. As an evaluation formula, the following equation (12) is used.

[Expression 12]

$$E_{idxture} = \sum_x \sum_y \{I_x^2(x, y) + I_y^2(x, y)\} \quad (12)$$

Note that $I_x(x,y)$ and $I_y(x,y)$ represent first derivations along the X- and Y-axes, respectively, when the pixel value at point (x,y) in the image is taken as I(x,y). Any block having a value of the evaluation formula which is equal to or more than a threshold value is determined to be a feature region, and any region which is similar to that of an adjacent image is searched for. With such a calculation method, it is possible to take, as a feature region, any portion where the sum of derivatives of the pixel values is large.

[(2) Modeling Inner Wall Motion of Digestive Organs]

As described above, the method that generates a large still image by reconstructing the movement of the camera from a sequence of successive images and pasting overlapping image regions is known as video mosaicking, and also known as a sprite compression method in MPEG-4. In the video mosaicking, a large background is previously transmitted, and small movement components constituting the foreground thereof are successively transmitted and reconstructed, thereby making it possible to efficiently reproduce a moving image. However, in the conventional video mosaicking, the camera motion is estimated by detecting how a fixed feature point or region in the background is moved on the image by moving the camera.

On the other hand, the inner walls of the small intestine and digestive apparatus ceaselessly repeat motion to send food or a capsule forward, and there is no fixed feature point. In addition, the inner walls are flexible objects and therefore expand and contract to some extent, but contraction of visceral muscle fibers forms soft plicae. Thus, it is difficult to apply the conventional approach as it is to generate a still image.

Therefore, in the present invention, a spread image of the inner wall of a digestive apparatus is generated by reconstructing the movement of the camera with respect to the inner wall of the digestive apparatus that involves motion and performing pasting to a still image while virtually stopping the motions of the camera and the inner wall of the digestive apparatus. In order to produce a highly accurate spread image, a video picture in a temporal section where an apparent image taken by the camera does not significantly change between successive frames.

First, motions in images of a sequence of successive images can be classified into those due to movement of the camera and those due to motion of the inner wall of the digestive apparatus. Among them, as for the movement of the camera, the camera itself may face various directions because there are no restrictions on the movement, whereas as for the motion of the inner wall of the digestive apparatus, the motion is unique to each internal organ. Specifically, as for the small intestine for which the capsule endoscope is effective, the motion of the inner wall of the digestive apparatus can be expressed by segmentation and peristalsis movements. The segmentation movement is motion caused by adjacent circular muscles intermittently contracting at the same time, and changes of the inner wall of the small intestine due to the contraction of the circular muscles arranged at regular intervals can be approximated with function f including a sine wave of the equation (11) as in the first embodiment.

Figure 13:
FIG. 13 is a diagram illustrating the movement of a soliton to which the peristalsis movement in a digestive organ is modeled.

On the other hand, the peristalsis movement is motion caused by a combination of circular muscles and longitudinal muscles, and in order to send food forward, a solitary wave travels as shown in FIG. 13, rather than successive waves appear.

This wave is considered as a soliton f, which is a progressive wave having a constant speed and shape, and can be expressed by a KdV (Korteweg-de Vries) equation in the following equation (13), which is a nonlinear wave equation.

[Expression 13]

$$f_t + f_{xxx} + 6ff_x = 0 \qquad (13)$$

Here, $f_t$ denotes the first partial derivative of a function f with respect to t, $f_x$ denotes the first partial derivative of the function f with respect to x, and $f_{xxx}$ denotes the third partial derivative of the function f with respect to x.

When the speed in the traveling direction at a position x in the progressive direction and at time t is taken as c, a solution f indicated by the following equation (14) is conceived to be one solution.

[Expression 14]

$$f = f(x, t) = 3c \operatorname{sech}^2\left[\frac{\sqrt{c}\,(x - ct)}{2}\right] \qquad (14)$$

Figure 14:
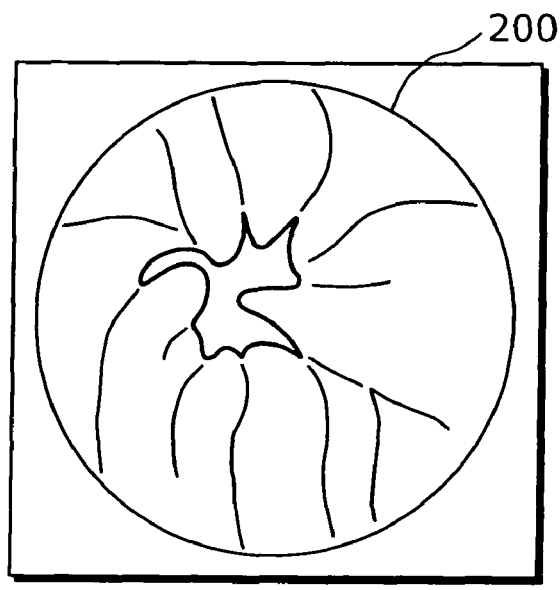
FIG. 14 is an illustration showing an exemplary image of the inner wall of the small intestine in which contraction of circular muscles is taking place.

The sine wave of the segmentation movement and the soliton of the peristalsis movement are not apparent motions from the camera, and therefore it is necessary to separate the sine wave and the soliton from variations in images obtained by the camera. For this separation, a feature on an image in which the segmentation movement and the peristalsis movement are considered to be taking place is used. In both the segmentation movement and the peristalsis movement, when the contraction of circular muscles occur, creases are generated along longitudinal muscles and radial creases as shown FIG. 14 appear at portions where the circular muscles contract. When such contraction occurs, it is conceivable that the segmentation movement or the peristalsis movement is taking place, and it is also conceivable that the past image continuous therewith has a movement component of the inner wall due to the segmentation movement or the peristalsis movement. However, in the state as shown in FIG. 14, the motion of the inner wall of the small intestine is excessively large and remarkably differs from that in the same region of an adjacent image with respect to how it appears, making it unusable for pasting. Accordingly, in several frames before the state of FIG. 14 appears, when the amount of movement of small regions, which is a variation due to contraction of an internal organ, is equal to or more than a threshold value, the subsequent image sequence is not used for pasting. Specifically, in the image sequence shown in FIG. 15, when the amount of movement of small regions 202 is equal to or more than a predetermined threshold value, subsequent images (images in section B of FIG. 15) are not used for pasting.

An image (an image 204 of FIG. 15) used for pasting in several frames before the state of FIG. 14 has a variation due to the segmentation movement or the peristalsis movement, and therefore image correction by a sine wave or a soliton is applied. Movements of the small intestine in images of other frames (images in section A of FIG. 15) are considered to be unmodeled minor movements and image variations due to the movement of the camera. Accordingly, images that are to be pasted are considered as corresponding to the state where there is almost no motion of the small intestine or a motion section in which the segmentation movement or the peristalsis movement is gentle.

Therefore, image pasting is carried out in accordance with the flowchart shown in FIG. 16.

Figure 15:
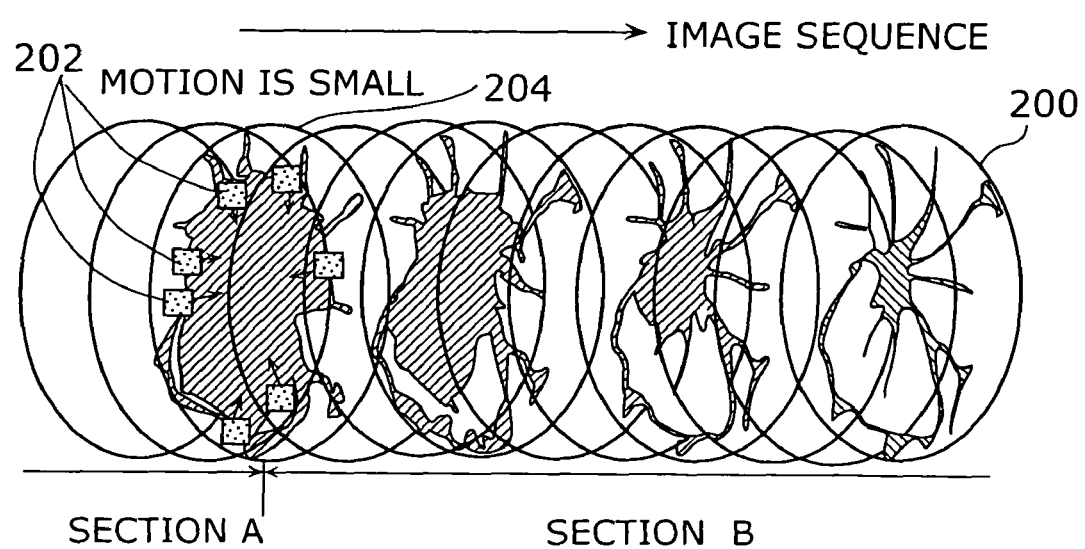
FIG. 15 is a diagram illustrating an exemplary image sequence in which the segmentation movement or the peristalsis movement is taking place.

First, an image corresponding to FIG. 14 is selected from all images in a sequence by image processing, and taken as a representative image (S1). This process is carried out by detecting the representative image in which the size of a dark portion, which is a cavity portion in front, is small and edge line segments indicating plicae radially extend from the dark portion as the center. Note that when a plurality of representative images are detected from a sequence of successive images as shown in FIG. 15, an image having the smallest dark portion is taken as a representative image 200.

Motion vectors of small regions 202 in past several frames of the representative image 200 are obtained between adjacent images, and when the length of the motion vectors is less than a threshold value, it is estimated that the segmentation movement or the peristalsis movement is at the initial stage (S2).

Since the sine wave of the segmentation movement and the soliton of the peristalsis movement in the image 204 of the initial stage vary depending on the direction of the camera, it is difficult to estimate an apparent waveform model, but it can be estimated that at the initial stage, all peripheral regions in the image slightly move toward the center of the small intestine. Accordingly, at the initial stage of the segmentation movement or the peristalsis movement (section A of FIG. 15), the average of movement components of image regions toward the center direction is obtained without distinguishing motions to modify the amount of movement (S3).

Thereafter, an energy minimization problem is applied to simultaneously carry out motion estimation of the camera and generation of a panoramic image (S4). At this time, minor deformation in the inner wall of the small intestine is also modified (S5). Note that the details of the energy minimization problem are described below.

[(3) Regarding the Energy Minimization Problem]

Further, feature regions obtained in accordance with the above-described evaluation formula (12) are taken as image control points and nationhood regions thereof to densely generate triangular patches having the control points as vertices on the image. Note that in the following description, the control point, when referred to as such, may imply a control point and its nationhood region.

FIGS. 17A and 17B are each a diagram illustrating exemplary triangular patches, in which FIG. 17A shows triangular patches in an f-th frame and FIG. 17B shows triangular patches in a (f+1)-th frame. As show in FIG. 17A, obtained feature regions $I_{k,f}$ (k is a feature region number, and f is a frame number) are densely connected to create triangular patches. The triangular patches are assigned a number such as m1 to m3.

When assuming that in adjacent images, a triangular patch in a past image is taken as the initial value and internal energy $E_{int}$ of a triangular patch is represented by the squared sum of differences in pixel value between control point neighborhood regions (feature regions) and the sum of differences in area between triangular patches, the internal energy $E_{int}$ of the triangular patch is defined as in the following equation (15).

[Expression 15]

$$E_{im} = \sum_{k}\left[\sum_{x}\sum_{y}\{I_{k,f}(x,y) - I_{k,f+1}(x,y)\}^2\right] + \sum_{m}(A_{m,f} - A_{m,f+1})^2 \quad (15)$$

Note that $A_{m,f}$ represents the area of a triangular patch formed from control points of a frame f. In addition, m represents a triangular patch number.

Specifically, the first term on the right-hand side of the internal energy $E_{int}$ of the triangular patch indicated by the equation (15) denotes the squared sum of differences in pixel between the control point neighborhood regions, and when the luminance distribution in the feature region is approximated between successive frames, the internal energy is small. The first term is also referred to as the "image energy".

In addition, the second term on the right-hand side denotes the sum of differences in area between triangular patches, and if variations in area between corresponding triangular patches in successive frames are small, i.e., the triangular patches are not deformed, the internal energy is small. The second term is also referred to as the "energy indicating a smoothness restriction".

Incidentally, the inside of a digestive tract is cylindrical. In addition, the omnidirectional camera HyperOmni Vision has the nature that all planes including a straight line passing through the viewpoint appear as a great circle in a spherical coordinate system with the viewpoint at its center. Based on this, external energy $E_{ext}$ is defined by the similarity between circles around the camera that are restructured between adjacent images. The circle similarity is defined based on the following equation (16), and the definition is established by the squared sum of distances from control point to great circle after a movement, such that the similarity becomes low when a plurality of great circles (3 to 5 circles) including three or more control points having a relatively large luminance value remain as the great circles after a movement.

[Expression 16]

$$E_{ext} = \sum_{n}\sum_{l}\{HC_{l,n,f} - C_{l,n,f+1}\}^2 \quad (16)$$

However, the camera moves constantly. Therefore, the transformation matrix due to the movement of the camera is defined as H. In addition, C denotes coordinates of a control point, l denotes a great circle number, and n denotes a number for a control point included in the great circle.

Accordingly, by obtaining a control point for minimizing the weighted sum of the internal energy and the external energy,

[Expression 17]

$$E = \Sigma\{\Delta E_{int} + (1-\alpha)E_{ext}\} \quad (17)$$

corresponding regions in adjacent images are obtained simultaneously with the camera motion, so that deformation between the adjacent images is obtained. Here, $\alpha$ is a constant from 0 to 1. By minimizing the energy E, it is made possible to cut out and paste images taken in a constant camera direction to generate a panoramic image.

Note that instead of the energy indicating a smoothness restriction indicated in the second term of the equation (15), the energy indicating a smoothness restriction indicated in the following equations (18) and (19) may be used. This energy refers to energy that is inclined to keep an adjacent control point at a constant distance.

Figure 18:
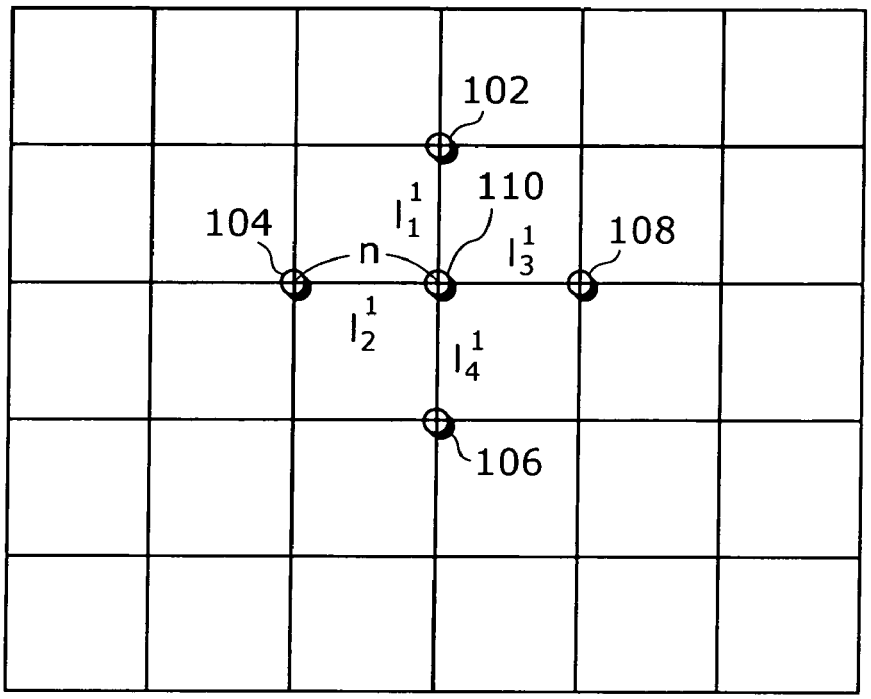
FIG. 18 is a diagram illustrating an image divided into meshes and control points on the image.

For example, as shown in FIG. 18, in the first frame, an image is divided into meshes. The pixel interval in the case where the image is divided into meshes is n pixels (n is a natural number).

Figure 19A:
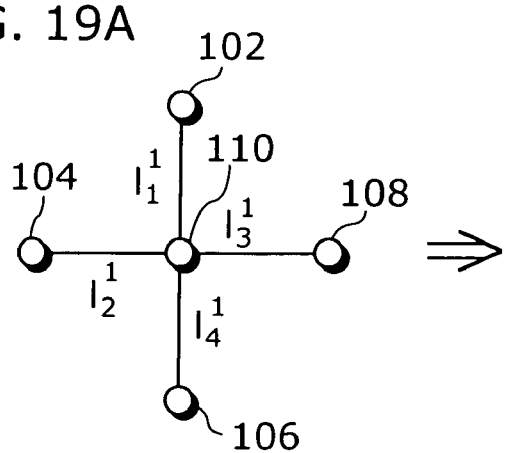
FIGS. 19A and 19B are illustrations showing the deformation of control points.
Figure 19B:
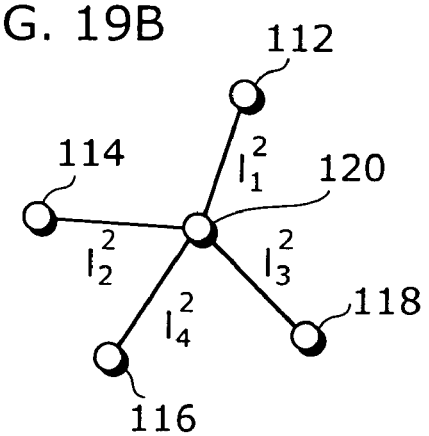

Five points (control points 102 through 110) are selected from control points on the meshes as shown in FIG. 19A, and the distances from the control point 110 at the center to the other four points are defined as $l_1^1$, $l_2^1$, $l_3^1$ and $l_4^1$.

Next, in the second frame, control points 112, 114, 116, 118 and 120 corresponding to the control points 102, 104, 106, 108 and 110, respectively, are obtained. The corresponding control points are obtained by normal pattern matching or the like.

Here, two types of energies are defined.

The energy indicated in the following equation (18) is energy that is minimized when the distances from the control point at the center to the other four points are equal to the pixel interval on the meshes, and by minimizing this energy, control points that are inclined to maintain the shape as shown in FIG. 19A are selected.

[Expression 18]

$$E(x) = \sum_{i}(l_i^t(x) - n)^2 \quad (18)$$

Here, t denotes a frame number, which indicates a number for a combination of control points. Note that such energy is obtained at a plurality of positions in an image, and the sum total of their energies may be obtained.

In addition, the energy indicated in the following equation (19) is energy that is minimized when four distances are equal to each other between the previous and current frames. By minimizing this energy, control points are selected so as to form an arrangement structure similar to that of control points in the previous frame.

[Expression 19]

$$E(x) = \sum_{i}(l_i^t(x) - l_i^{t-1}(x))^2 \quad (19)$$

By solving the above described energy minimization problem, it is made possible to associate control points between successive frames. Accordingly, by pasting images obtained in the respective frames, while deforming them, based on the association between triangular patches surrounded by control points, it is possible to obtain an image of the inside of a digestive tract that has been subjected to a video mosaicking process.

To summarize the foregoing, the amount of movement of the camera is obtained while associating identical minor regions between successive images of gently changing sections of a changing inner wall of the small intestine, excluding significantly contracting sections, and the images are deformed and pasted, such that the identical regions precisely overlap each other. Error caused in the estimation of the amount of camera movement is modified such that the images move entirely at the time of pasting, and images of regions around control points are pasted, while gently correcting the motion of the inner wall of the small intestine, to generate a spread image of the inner wall of the small intestine.

As described above, according to the present embodiment, the shape of the inside of the digestive tract and the motion of the camera are expressed as model parameters, and control points are moved to positions where energy utilizing these model parameters is minimized, so that the control points can be associated. Therefore, by utilizing the association between the control points, it is possible to generate a panoramic image. In the first embodiment, estimation of camera motion and pasting of images are carried out in separate processes. Therefore, in the case where the estimation of camera motion is erroneous, the pasting of images might not be successful, but such does not occur in the second embodiment.

While an endoscope system according to the present invention has been described with respect to an embodiment, the present invention is not limited to this embodiment.

For example, the model formula (equation 13) for the peristalsis movement described in the embodiment may be applied to the first embodiment to carry out a bundle adjustment process for correcting the camera motion.

In addition, an omnidirectional mirror may be mounted to an existing endoscope as an attachment to realize omnidirectional vision.

In addition, the omnidirectional camera may use a mirror other than a hyperboloidal mirror, such as a cone mirror, a spherical mirror, a parabolic mirror or the like. Moreover, it may be a combination of a plurality of such mirrors.

In addition, the present invention is not limited to the examination of intestinal tracts, and may be used for examination of other internal organs, intravascular examination and the like. For example, the present invention may be applied to micromachine technology, such as a system for taking an image of the inside of a blood vessel.

In addition, it may be applied to examination of the inside of any movable tubular object in a living body, such as a nostril, an ear hole, an oral cavity, the inside of the vagina, the inside of the bladder and the urethra.

Further, a camera may be mounted to the tip of a catheter to apply the technology of the present invention to examination of the inside of the heart, the intravascular examination and so on.

Furthermore, a camera may be mounted to the tip of a laparoscope, which is a type of the endoscope, to apply the technology of the present invention to examination of organs such as the esophagus, stomach, duodenum, gallbladder, bile duct, vermiform appendix, thyroid grand, mammary gland and lung.

INDUSTRIAL APPLICABILITY

The present invention is applicable to endoscopes, and in particular to a probe-type endoscope or a capsule endoscope.

The invention claimed is:

1. An endoscope system for taking images of an inside of an object, comprising:
    an omnidirectional camera operable to take a plurality of images of the inside of the object in a living body, which is capable of motion; and
    an image generation unit operable to generate a panoramic image of the inside of the object by performing a video mosaicking process, a motion correction process, and an image modification process through energy minimization on the plurality of images obtained by said omnidirectional camera, said processes being intended for pasting the images, estimating camera motion, correcting previously definable motion in the living body, and correcting previously indefinable internal deformation in the living body,
    wherein said image generation unit is operable to generate the panoramic image such that the panoramic image has a fixed visual angle with respect to each of directions perpendicular to a traveling direction of said omnidirectional camera, by performing the video mosaicking process on the plurality of images obtained by said omnidirectional camera,
    wherein said image generation unit includes:
        a feature region cutout unit operable to cut out a plurality of feature regions having a predetermined size from each of the plurality of images obtained by said omnidirectional camera; and
        a panoramic image generation unit operable to define energy based on the plurality of feature regions included in each of the plurality of images, associate the plurality of feature regions between the plurality of images such that the energy is minimized, and generate a panoramic image of the inside of the object based on the association result, and
    wherein the plurality of feature regions are regions which are included in the plurality of regions having the predetermined size included in each of the images, and in which a squared sum of derivatives of pixel values is greater than a predetermined threshold value.

2. The endoscope system according to claim 1,
    wherein the energy is determined based on differences in pixel value between the plurality of feature regions included in each of two temporally successive images.

3. The endoscope system according to claim 1,
    wherein the energy is determined based on differences in area between triangular patches obtained by connecting the plurality of feature regions included in each of two temporally successive images.

4. The endoscope system according to claim 1,
    wherein the energy is determined based on a difference between (i) a coordinate obtained by correcting, based on a movement component of said omnidirectional camera, a coordinate of a great circle which appears in an image after a first image taken by said omnidirectional camera is transformed in a spherical coordinate system with its center at a viewpoint of said omnidirectional camera, and (ii) a coordinate of a great circle which appears in an image after a second image temporally successive to the first image and taken by said omnidirectional camera is transformed in the spherical coordinate system.

5. The endoscope system according to claim 1,
    wherein the energy is determined based on a degree of deviation of a plurality of control points, in a second image taken by said omnidirectional camera, which respectively correspond to a plurality of control points selected from a first image taken by said omnidirectional camera.

6. The endoscope system according to claim 1, wherein the energy is determined based on a degree of deviation between a plurality of control points selected from a first image taken by said omnidirectional camera and a plurality of control points, in a second image taken by said omnidirectional camera, which respectively correspond to the plurality of control points selected from the first image.

7. The endoscope system according to claim 1, wherein said omnidirectional camera is mounted on a tip of a probe that is to be inserted into a digestive organ.

8. The endoscope system according to claim 1, wherein said omnidirectional camera is enclosed in a capsule that can be swallowed by a human or an animal.

9. An endoscope system for taking images of an inside of an object, comprising:
a camera operable to take a plurality of images of the inside of the object in a living body, which is capable of motion; and
an image generation unit operable to generate a panoramic image of the inside of the object by performing a video mosaicking process, a motion correction process, and an image modification process through energy minimization on the plurality of images obtained by said camera, said processes being intended for pasting the images, estimating camera motion, correcting previously definable motion in the living body, and correcting previously indefinable internal deformation in the living body,
wherein said image generation unit includes:
a feature region cutout unit operable to cut out a plurality of features regions having a predetermined size from each of the plurality of images obtained by said camera; and
a panoramic image generation unit operable to define energy based on the plurality of feature regions included in each of the plurality of images, associate the plurality of feature regions between the plurality of images such that the energy is minimized, and generate a panoramic image of the inside of the object based on the association result, wherein the plurality of feature regions are regions which are included in the plurality of regions having the predetermined size included in each of the images, and in which a squared sum of derivatives of pixel values is greater than a predetermined threshold value.

* * * * *